United States Patent
Sunagawa et al.

(10) Patent No.: US 8,946,688 B2
(45) Date of Patent: Feb. 3, 2015

(54) POLYCYCLIC RING-FUSED COMPOUND AND ORGANIC THIN FILM TRANSISTOR UTILIZING THE SAME

(75) Inventors: Misa Sunagawa, Sodegaura (JP); Masatoshi Saito, Sodegaura (JP); Hiroaki Nakamura, Sodegaura (JP); Hirofumi Kondo, Sodegaura (JP); Naoki Kurihara, Sodegaura (JP); Masahiro Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 263 days.

(21) Appl. No.: 13/514,453

(22) PCT Filed: Dec. 13, 2010

(86) PCT No.: PCT/JP2010/007220
§ 371 (c)(1),
(2), (4) Date: Jul. 16, 2012

(87) PCT Pub. No.: WO2011/074232
PCT Pub. Date: Jun. 23, 2011

(65) Prior Publication Data
US 2012/0273770 A1    Nov. 1, 2012

(30) Foreign Application Priority Data

Dec. 14, 2009  (JP) .................................. 2009-283280

(51) Int. Cl.
*H01L 51/30* (2006.01)
*H01L 51/00* (2006.01)
(Continued)

(52) U.S. Cl.
CPC .......... *H01L 51/0072* (2013.01); *C07D 487/04* (2013.01); *C07D 493/04* (2013.01);
(Continued)

(58) Field of Classification Search
USPC .......................................................... 257/40
See application file for complete search history.

(56) References Cited

U.S. PATENT DOCUMENTS

| 5,936,259 A | 8/1999 | Katz et al. |
| 6,768,132 B2 * | 7/2004 | Smith et al. ..................... 257/40 |

(Continued)

FOREIGN PATENT DOCUMENTS

| JP | 11-195790 A | 7/1999 |
| JP | 2009-267134 A | 11/2009 |
| TW | 200917543 A | 4/2009 |

OTHER PUBLICATIONS

88th, Spring Meeting of Japan Chemical Society, 2008, preprint for meeting 3K1-02.
(Continued)

*Primary Examiner* — Eugene Lee
(74) *Attorney, Agent, or Firm* — Foley & Lardner LLP

(57) ABSTRACT

A compound for an organic thin film transistor represented by the following formula (1):

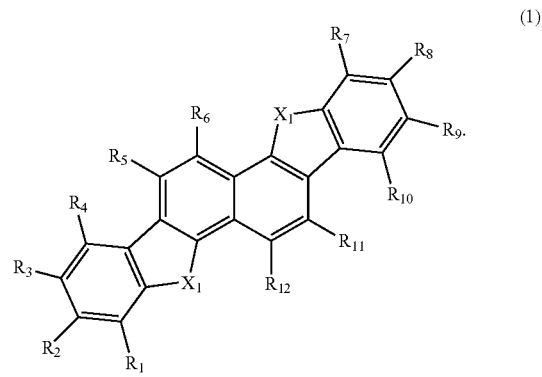

14 Claims, 2 Drawing Sheets

(51) Int. Cl.
*C07D 487/04* (2006.01)
*C07D 493/04* (2006.01)
*H01L 51/05* (2006.01)

(52) U.S. Cl.
CPC ......... *H01L51/0073* (2013.01); *H01L 51/0541* (2013.01); *H01L 51/0545* (2013.01); *H01L 51/0558* (2013.01)
USPC .......................................................... 257/40

(56) References Cited

U.S. PATENT DOCUMENTS

| | | | | |
|---|---|---|---|---|
| 7,968,872 | B2* | 6/2011 | Schafer et al. | 257/40 |
| 8,030,645 | B2* | 10/2011 | Takeuchi et al. | 257/40 |
| 8,101,776 | B2* | 1/2012 | Berens et al. | 548/148 |
| 8,441,002 | B2* | 5/2013 | Murase et al. | 257/40 |
| 2004/0131880 | A1 | 7/2004 | Zheng et al. | |
| 2010/0187514 | A1 | 7/2010 | Nakano et al. | |
| 2012/0012822 | A1* | 1/2012 | Kakiuchi et al. | 257/40 |
| 2012/0097935 | A1* | 4/2012 | Kirner et al. | 257/40 |

OTHER PUBLICATIONS

Fabien Dufour et al., "Carbazolo[2,1-*a*] carbazole Derivatives via Fischer Indole Synthesis", Journal of Heterocyclic Chemistry, 2008, pp. 161-163, vol. 45, No. 1.

H. S. Desai et al., "Thipohenes & Thiapyrans: Part XXV-Condensed Thiophenes & Thiapyrans from I,5-, I,4- & I,3-Dimercaptonaphthalenes", Journal of Scientific & Industrial Research, Jan. 1961, pp. 1-42, vol. 20B, No. 1.

Norbert Haider et al., "Diels-Alder Reaction of Pyrano[3,4-*b*]Indolones With An Electron-Deficient Pyridazinone: A New Pathway to Carbazole-Fused Pyridazines", Heterocycles, 1999, pp. 2703-2710, vol. 51, No. 11.

International Search Report received in International Application No. PCT/JP2010/007220 dated Jan. 18, 2011.

Written Opinion received in International Application No. PCT/JP2010/007220 dated Jan. 18, 2011.

Taiwanese Office Action dated Oct. 14, 2014 issued in Application No. 099143821.

* cited by examiner

POLYCYCLIC RING-FUSED COMPOUND AND ORGANIC THIN FILM TRANSISTOR UTILIZING THE SAME

CROSS-REFERENCE TO RELATED APPLICATIONS

This application is a National Stage application of PCT/JP2010/007220, filed Dec. 13, 2010, which claims priority from Japanese application JP 2009-283280 filed Dec. 14, 2009.

TECHNICAL FIELD

The invention relates to a polycyclic ring-fused compound and an organic thin film transistor using the same.

BACKGROUND ART

A thin film transistor (TFT: Thin Film Transistor) has been widely used as a switching device for a display for a liquid crystal display device or the like. A representative TFT has a configuration in which a gate electrode, an insulator layer and a semiconductor layer are stacked in this sequence on a substrate, and has, on the semiconductor layer, a source electrode and a drain electrode being formed with a predetermined interval therebetween. The organic semiconductor layer constitutes a channel part, and an on-off operation is conducted by controlling electric current flowing between the source electrode and the drain electrode by a voltage applied to the gate electrode.

Conventionally, this TFT was fabricated by using amorphous or polycrystalline silicon. However, a CVD (chemical vapor deposition) apparatus used for fabrication of a TFT using silicon is very expensive, and an increase in size of a display or the like using a TFT had a problem that the production cost increased significantly. Further, there was a problem that, since forming amorphous or polycrystalline silicon into a film requires significantly high temperatures, the type of a material which is usable as a substrate is limited, and hence, there were also problems that resin substrates or the like which were light in weight could not be used.

In order to solve the problem, a TFT using an organic substance (hereinafter often referred to as an organic TFT) instead of amorphous or polycrystalline silicon has been proposed. As the film-forming method which is used when a TFT is fabricated by using an organic substance, a vacuum vapor deposition method, a coating method or the like are known. According to these methods, it is possible to realize an increase in size of a device while suppressing an increase in the production cost, and is also possible to allow the process temperature which is required at the time of film formation to be relatively low. Accordingly, in such an organic TFT, there are advantages that only small restrictions are imposed on the type of materials used for a substrate. Therefore, its practical use has been expected and research reports have been actively made.

A practical organic TFT is required to have a high carrier mobility (hereinafter often referred to as the "mobility"), a large on-off ratio of current and excellent storage stability. Meanwhile, the on-off ratio refers to herein a value which is obtained by dividing a current flowing between source and drain electrodes when a gate voltage is applied (ON) by a current flowing between source and drain electrodes when a gate voltage is not applied (OFF). The on-current normally means a current value at the time when the current flowing between source and drain electrodes is saturated (saturation current) after increasing the gate voltage.

As a p-type organic semiconductor material used in an organic TFT, a polymer such as a conjugated polymer or thiophene, metal phthalocyanine compounds, and fused aromatic hydrocarbons such as pentacene or the like have been known. However, an organic semiconductor material which satisfies all of the required performances has not yet been developed.

Of the above-mentioned organic semiconductors, pentacene, which is a polycyclic ring-fused compound, has attracted attention as a material which has a mobility as high as that of amorphous silicon due to its conjugated system, and has been actively studied. However, pentacene has a disadvantage that the stability in the atmosphere is low.

Under such circumstances, as the material which has storage stability and has high carrier mobility, various polycyclic ring-fused compounds have been studied.

For example, a polycyclic ring-fused compound having five rings in which two benzofuran skeletons are fused to the benzene ring was reported in a meeting as an effective compound since it has a carrier mobility of on the order of $2\times10^{-1}$ cm$^2$/Vs (Non-Patent Document 1). Further, a polycyclic ring-fused compound having four rings in which two furan rings are fused to the naphthalene ring or a polycyclic ring-fused compound having five rings in which two furan rings are fused to the anthracene ring has been proposed as a material of an organic semiconductor layer of an organic TFT. However, no specific examples or the like have been made on a polycyclic compound having 6 rings (Patent Document 1).

Further, the following compounds have been synthesized (Non-Patent Documents 2 to 4). However, the performance as the organic semiconductor material has not yet been demonstrated.

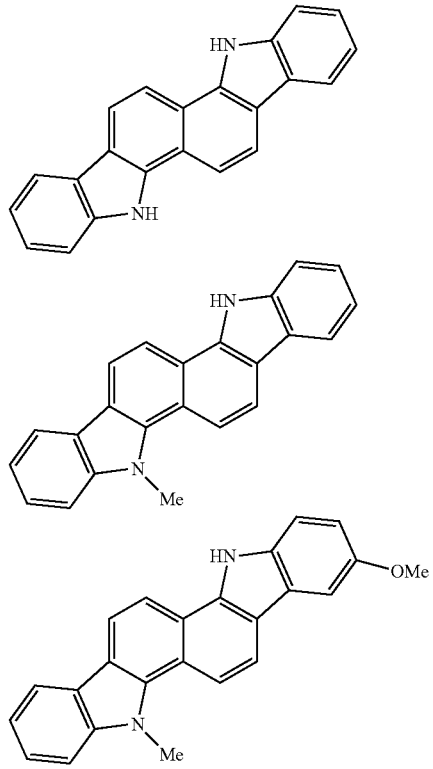

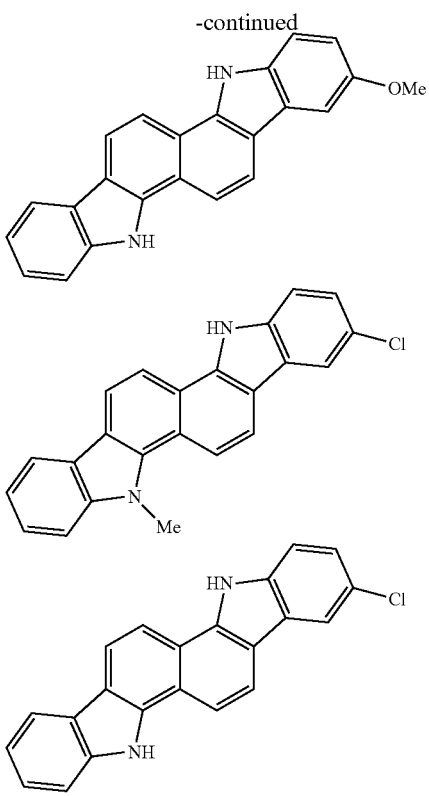

RELATED ART DOCUMENTS

Patent Document

Patent Document 1: JP-A-H11-195790

Non-Patent Documents

Non-Patent Document 1: 88th, Spring Meeting of Japan Chemical Society (2008), preprint for meeting 3K1-02
Non-Patent Document 2: Heterocycles, 51, 2703 (1999)
Non-Patent Document 3: Journal of Scientific & Industrial Research, 20B, 22 (1961)
Non-Patent Document 4: Journal of Heterocyclic Chemistry, 45, 161 (2008)

SUMMARY OF THE INVENTION

As mentioned above, since a polycyclic ring-fused compound can be a material which has a further higher carrier mobility due to the π-conjugated system thereof, development of a novel polycyclic ring-fused compound has been desired.

An object of the invention is to provide a novel material for an organic thin film transistor which has a high carrier mobility.

As the result of studies made on various polycyclic ring-fused compounds, the inventors have found a polycyclic ring-fused compound having 6 rings in which the π-conjugated system of the compound is expanded by further fusing an aromatic ring to the naphthalene ring is effective as a material for an organic TFT.

According to the invention, the following compound for an organic thin film transistor or the like is provided.

1. A compound for an organic thin film transistor represented by the following formula (1):

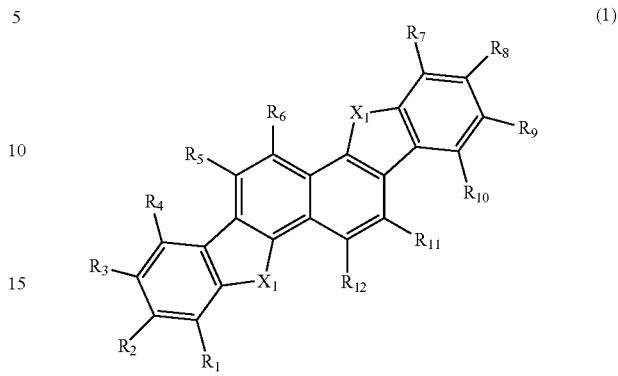

wherein $X_1$s are independently an oxygen atom or a group represented by N—$R_{13}$;

$R_1$ to $R_{13}$ are independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent; and when $X_1$s are both groups represented by N—$R_{13}$, two $R_{13}$s may be the same or different.

2. A polycyclic ring-fused compound represented by the following formula (2):

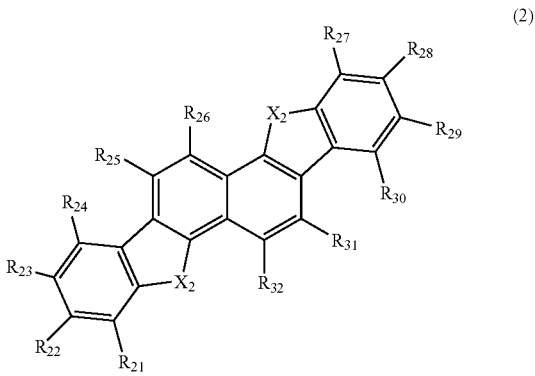

wherein $X_2$s are independently an oxygen atom or a group represented by N—$R_{33}$;

$R_{21}$ to $R_{32}$ are independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent;

$R_{33}$ is a halogen atom, an alkyl group having 1 to 30 carbon atoms, a haloalkyl group having 1 to 30 carbon atoms, an alkoxy group having 1 to 30 carbon atoms, a haloalkoxy group 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent; and when $X_2$s are both groups represented by $N-R_{33}$, two $R_{33}$s may be the same or different.

3. A material for an organic thin film transistor comprising the compound represented by the formula (1) or (2) according to 1 or 2.
4. An organic thin film transistor comprising at least three terminals of a gate electrode, a source electrode and a drain electrode, an insulating layer and an organic semiconductor layer provided on a substrate, current flowing between the source electrode and the drain electrode being controlled by applying a voltage to the gate electrode, the organic semiconductor layer comprising the compound represented by the formula (1) or (2) according to 1 or 2.
5. The organic thin film transistor according to 4, wherein light is emitted by utilizing current flowing between the source electrode and the drain electrode and emission is controlled by applying a voltage to the gate electrode.
6. The organic thin film transistor according to 5, wherein one of the source electrode and the drain electrode comprises a material having a work function of 4.2 eV or more and the other electrode comprises a material having a work function of 4.3 eV or less.
7. The organic thin film transistor according to any of 4 to 6, which further comprises a buffer layer between the source and drain electrodes, and the organic semiconductor layer.
8. An apparatus comprising the organic thin film transistor according to any of 4 to 7.

According to the invention, a novel material for an organic thin film transistor having a high carrier mobility can be provided.

MODE FOR CARRYING OUT THE INVENTION

Figure 1:
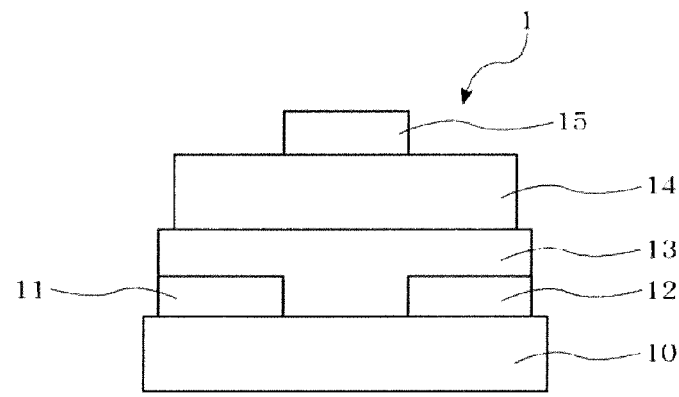
FIG. 1 is a view showing one example of the device configuration of the organic thin film transistor of the invention.

The compound for an organic thin film transistor of the invention is represented by the following formula (1):

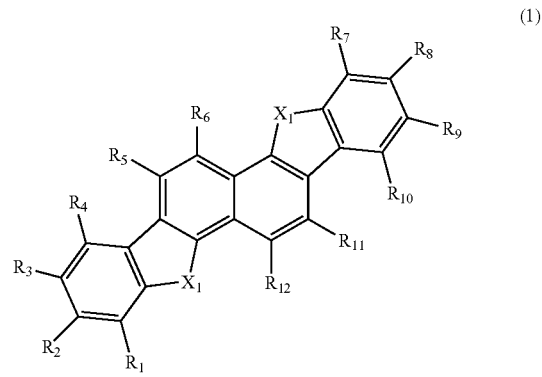

(1)

In the formula (1), $X_1$s are independently an oxygen atom or a group represented by $N-R_{13}$.

$R_1$ to $R_{13}$ are independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent.

If $R_{13}$ is an alkyl group or an aryl group, the compound is preferable to be used as the semiconductor material for the organic thin film transistor, since the stability of the compound can be kept, and at the same time, the π-conjugated systems among the molecules are appropriately overlapped, thereby enabling the carrier mobility to be improved.

When $X_1$s are both groups represented by $N-R_{13}$, two $R_{13}$s may be the same or different.

The polycyclic ring-fused compound of the invention is represented by the following formula (2). This compound is included in the compounds represented by the formula (1).

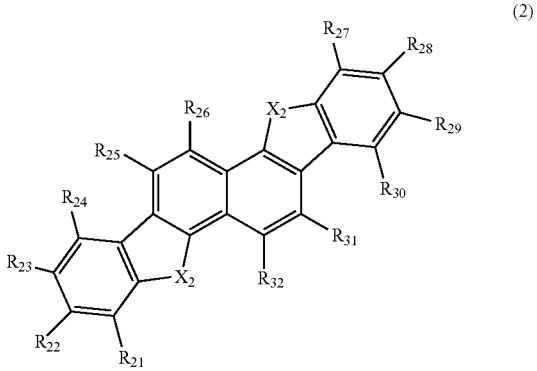

(2)

In the formula (2), $X_2$s are independently an oxygen atom or a group represented by N—$R_{33}$, $R_{21}$ to $R_{32}$ are independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent.

$R_{33}$ is a halogen atom, an alkyl group having 1 to 30 carbon atoms, a haloalkyl group having 1 to 30 carbon atoms, an alkoxy group having 1 to 30 carbon atoms, a haloalkoxy group 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent.

If $R_{33}$ is an alkyl group or an aryl group, the compound is preferable to be used as the semiconductor material for the organic thin film transistor, since the stability of the compound can be kept, and at the same time, the π-conjugated systems among the molecules are appropriately overlapped, thereby enabling the carrier mobility to be improved.

When $X_2$s are both groups represented by N—$R_{33}$, two $R_{33}$s may be the same or different.

Since the compound of the invention has a phenacene-type structure, it is expected to have excellent storage stability as compared with a compound having an acene-type structure.

In the formulas (1) and (2), compounds having a substituent can be applied to a solution process in which the compound of the invention is dissolved in a solvent to form an organic semiconductor layer, and hence, preferable in respect of diversification of a method for producing an organic TFT. A linear substituent is more preferable.

As the semiconductor material for an organic TFT, in the formula (1) or (2), the interaction between molecules by Van der Waals force due to the side chain and the freedom in change of conformation of the side chain are thought to affect the solubility. Therefore, in order to impart the compound with solubility while keeping a high mobility, it is important to introduce an appropriate substituent at an appropriate position of a polycyclic ring-fused compound without impairing the crystallinity in the solid state.

In this respect, it is preferred that a linear substituent be introduced at the positions of $R_1$ to $R_{12}$ in the formula (1) and the positions of $R_{21}$ to $R_{32}$ in the formula (2).

As for a substituent containing an alkyl chain such as an alkyl group, a haloalkyl group, an alkoxy group and an alkylthio group, the solubility of the compound is expected to be increased by using a branched alkyl group.

On the other hand, a shorter alkyl group is expected to allow the heat resistance of a device to be increased. A longer alkyl group enables dense packing of crystals due to the interaction of alkyl chains, and as a result, there is a possibility that the mobility of a device is improved. Taking this into consideration, an alkyl chain having a suitable length, for example, an alkyl chain having about 4 to 15 carbon atoms is preferable.

Hereinafter, specific examples of each group represented by $R_1$ to $R_{13}$ in the formula (1) and $R_{21}$ to $R_{33}$ in the formula (2) will be explained.

As the halogen atom, a fluorine atom, a chlorine atom, a bromine atom and an iodine atom can be given.

As the alkyl group, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosane group, an n-heneicosane group, an n-docosane group, an n-tricosane group, an n-tetracosane group, an n-pentacosane group, an n-hexacosane group, an n-heptacosane group, an n-octacosane group, an n-nonacosane group, an n-triacosane group or the like can be given.

Specific examples of the haloalkyl group include a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a fluoromethyl group, a 1-fluoroethyl group, a 2-fluoroethyl group, a 2-fluoroisobutyl group, a 1,2-difluoroethyl group, a difluoromethyl group, a trifluoromethyl group, a pentafluoroethyl group, a perfluoroisopropyl group, a perfluorobutyl group and a perfluorocyclohexyl group.

The alkoxy group is a group represented by —$OY^1$, and the examples of $Y^1$ include the same groups as those exemplified in the above-mentioned alkyl group. The haloalkoxy group is a group represented by —$OY^2$, and the examples of $Y^2$ include the same groups as those exemplified in the above-mentioned haloalkyl group.

The alkylthio group is a group represented by —SY¹, and the examples of Y¹ include the same groups as those exemplified in the above-mentioned alkyl group. The haloalkylthio group is a group represented by —SY², and the examples of Y² include the same groups as those exemplified in the above-mentioned haloalkyl group.

The alkylamino group is a group represented by —NHY¹, and the dialkylamino group is a group represented by —NY¹Y³, and the examples of Y¹ and Y³ include the same groups as those exemplified in the above-mentioned alkyl group. The alkyl groups of the dialkylamino group may combine with each other to form a ring structure containing a nitrogen atom. Examples of the ring structure include pyrrolidine, piperidine, or the like.

The alkylsulfonyl group is a group represented by —SO₂Y¹. The examples of Y¹ include the same groups as those exemplified in the above-mentioned alkyl group. The haloalkylsulfonyl group is a group represented by —SO₂Y². The examples of Y² include the same groups as those exemplified in the above-mentioned haloalkyl group.

The aryl group is an aromatic hydrocarbon ring and an aromatic heterocyclic ring. Specific examples of the aromatic hydrocarbon ring include benzene, naphthalene, anthracene, chrysene, phenanthrene, tetracene, fluorene, pyrene, fluoranthene and perylene. As the specific examples of the aromatic heterocyclic group, pyridine, pyrazine, indole, acridine, pyrrole, imidazole, pyrazole, quinoline, naphthylizine, quinoxaline, phenazine, phenothiazine, phenoxazine, diaza-anthracene, pyridoquinoline, pyrimidoquinazoline, pyrazinoquinoxaline, phenanthroline, carbazole, thiophene, benzothiophene, dibenzothiophene, benzodithiophene, [1]benzothieno[3,2-b]benzothiophene, thienothiophene, dithienothiophene, furan, benzofuran, dibenzofuran, benzodifuran, thiazole, benzothiazole, dithiaindacene, dithiaindenoindene, dibenzoselenophene, diselenaindacene, diselenaindenoindene and dibenzosilole can be given.

The alkylsilyl group is a group represented by —SiY¹Y³Y⁴ and the examples of Y¹, Y³ and Y⁴ include the same groups as exemplified in the above-mentioned alkyl group. A trimethylsilyl group or the like can be given, for example.

The alkylsilylethynyl group is a group in which the alklyl-silyl groups are combined via an ethynylene group, and a trimethylsilylethynyl group, a triethylsilylethynyl group and a triisopropylsilylethynyl group, or the like can be given.

The arylamino group is a group represented by —NHY⁵, and the diarylamino group is a group represented by —NY⁵Y⁶. The examples of Y⁵ and Y⁶ include the same groups as exemplified in the above-mentioned aryl group.

Substituents which may be further substituted on the substituent which is each group represented by $R_1$ to $R_{13}$ in the formula (1) and $R_{21}$ to $R_{33}$ in the formula (2) include, in addition to an aromatic hydrocarbon group, an aromatic heterocyclic group, an alkyl group, an alkoxy group, a haloalkyl group, an alkylthio group and an alkylsulfonyl group, an aryloxy group, an arylthio group, an alkoxycarbonyl group, an amino group, a halogen atom, a cyano group, a nitro group, a hydroxyl group and a carboxyl group.

The organic compound having a specific structure which is used in the organic thin film transistor of the invention is basically a bipolar compound showing both p-type performance (hole conductance) and n-type performance (electron conductance). In combination with a source electrode and a drain electrode mentioned later, the transistor can be driven both as a p-type device and an n-type device.

By using an electron-accepting group as $R_1$ to $R_{13}$ in the formula (1) and $R_{21}$ to $R_{33}$ in the formula (2), the lowest unoccupied molecular orbital (LUMO) level is decreased, thus enabling the compound to serve as an n-type semiconductor. Preferable examples of the electron-accepting group include a hydrogen atom, a halogen atom, a cyano group, a haloalkyl group having 1 to 30 carbon atoms, a haloalkoxy group having 1 to 30 carbon atoms, and a haloalkylsulfonyl group having 1 to 30 carbon atoms. Further, by using an electron-donating group as $R_1$ to $R_{13}$ in the formula (1) and $R_{21}$ to $R_{33}$ in the formula (2), the highest occupied molecular orbital (HOMO) is increased, thus enabling the compound to serve as a p-type semiconductor. Preferable examples of the electron-donating group include a hydrogen atom, an alkyl group having 1 to 30 carbon atoms, an alkoxy group having 1 to 30 carbon atoms, an alkylamino group having 1 to 30 carbon atoms and a dialkylamino group having 2 to 60 carbon atoms wherein the amino groups may be combined with each other to form a ring structure containing a nitrogen atom.

Hereinbelow, the specific examples of the polycyclic ring-fused compound which can be advantageously used in the organic thin film transistor of the invention are given below. The invention is, however, not limited thereto. The "N—" in the compounds represented by (B-1) or the like means "N—CH₃".

A-1

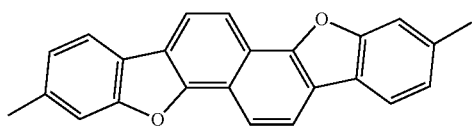

A-2

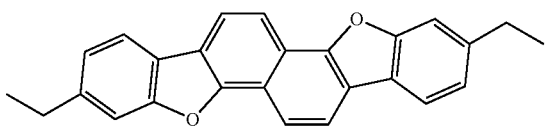

A-3

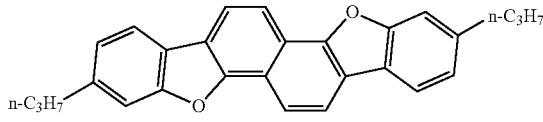

A-4

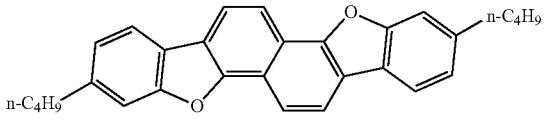

A-5

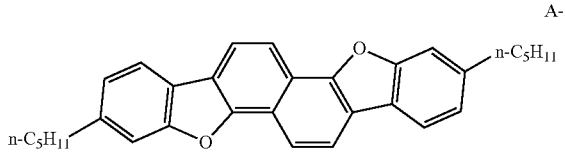

A-6

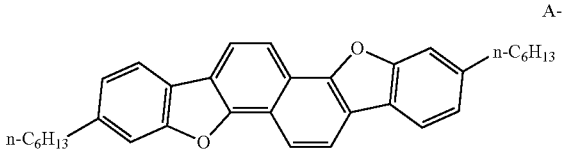

-continued
A-7
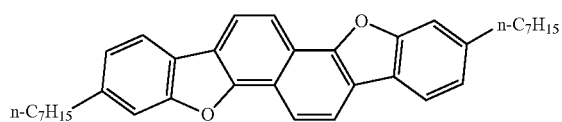
A-8
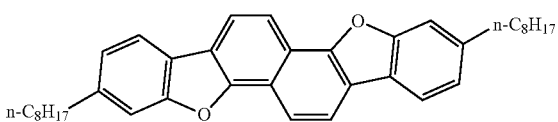
A-9
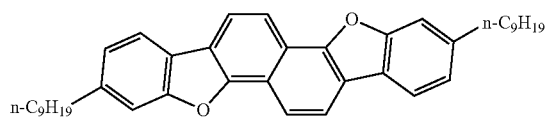
A-10
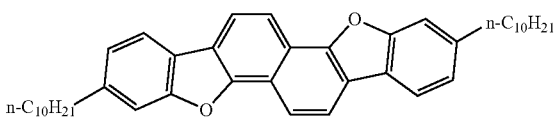
A-11
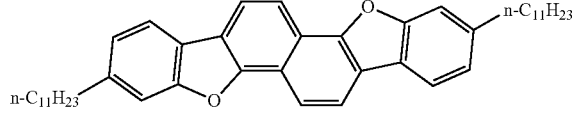
A-12
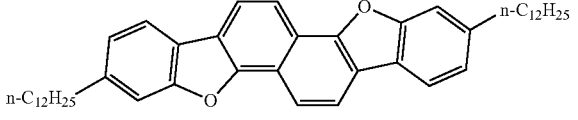
A-13
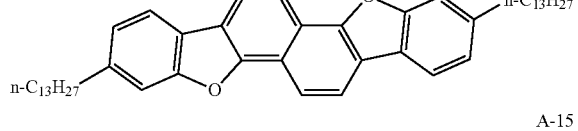
A-14
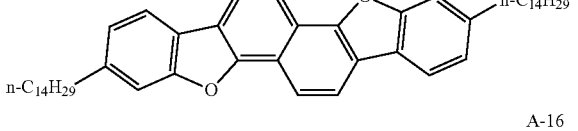
A-15
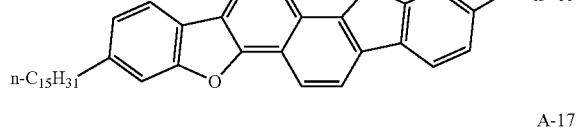
A-16
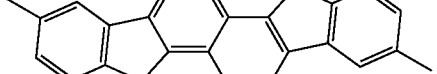
A-17
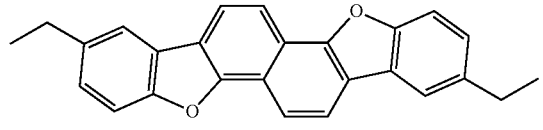
A-18
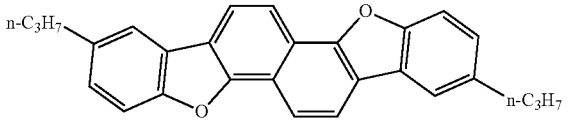
A-19
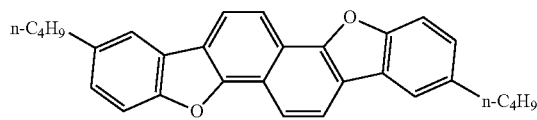
A-20
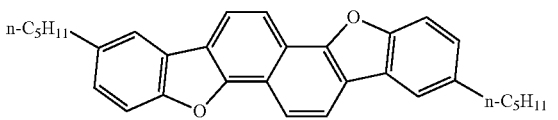
A-21
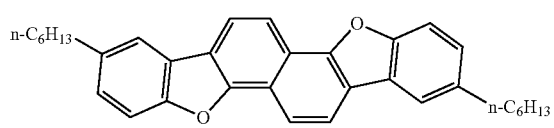
A-22
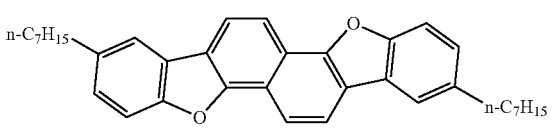
A-23
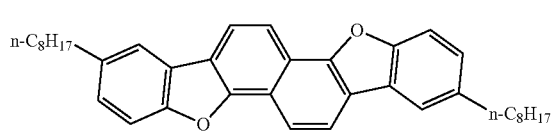
A-24
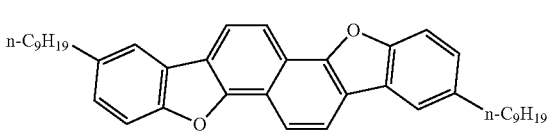
A-25
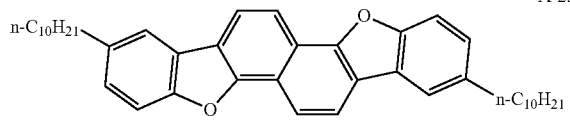
A-26
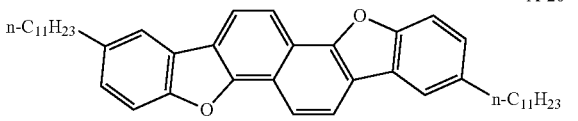
A-27
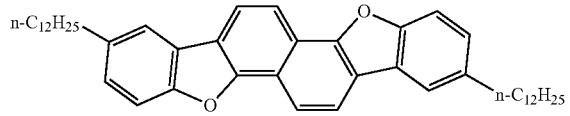
A-28
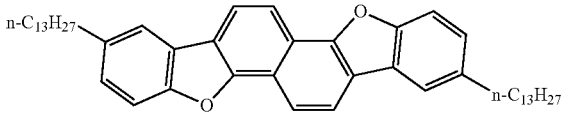

-continued
A-29
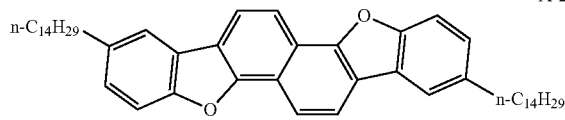
A-30
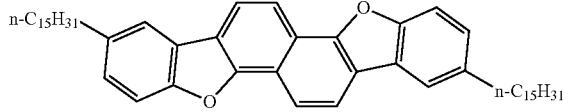
A-31
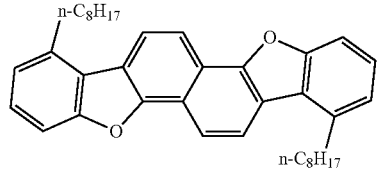
A-32
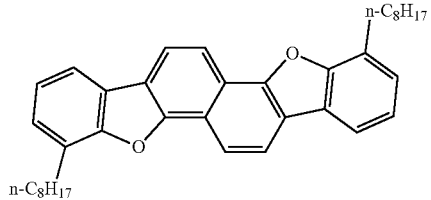
A-33
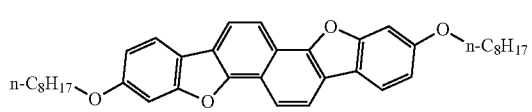
A-34
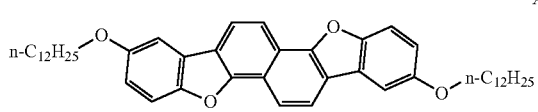
A-35
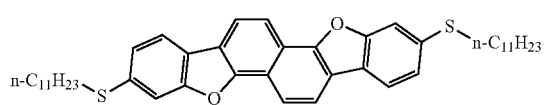
A-36
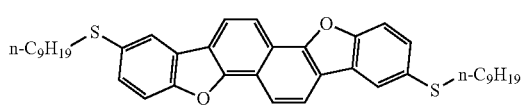
A-37
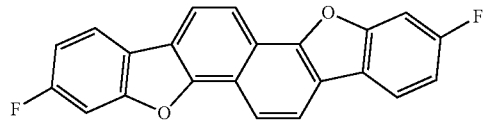
A-38
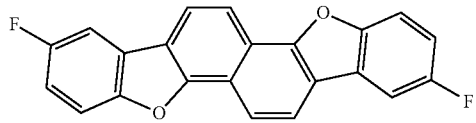
A-39
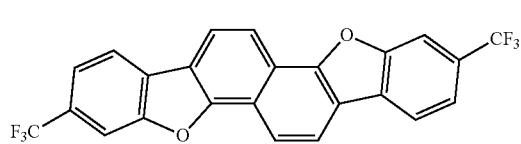
A-40
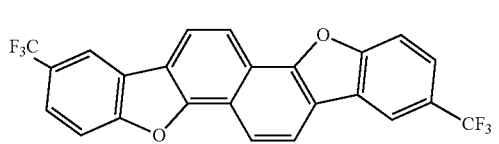
A-41
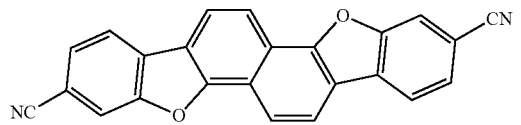
A-42
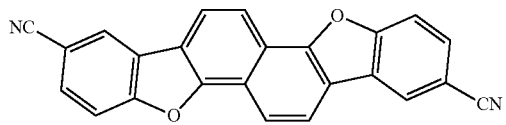
A-43
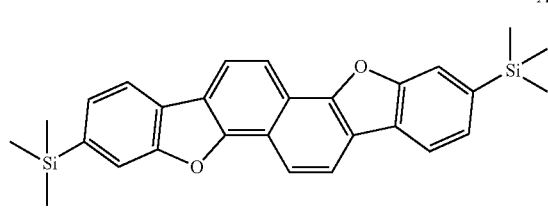
A-44
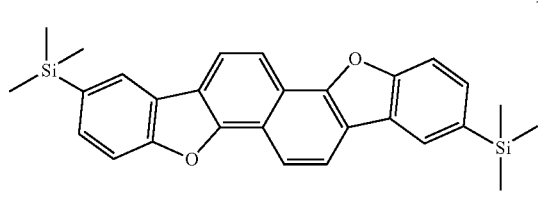
A-45
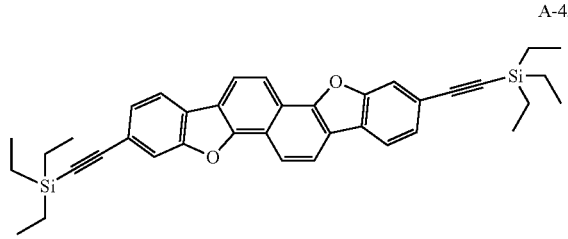
A-46
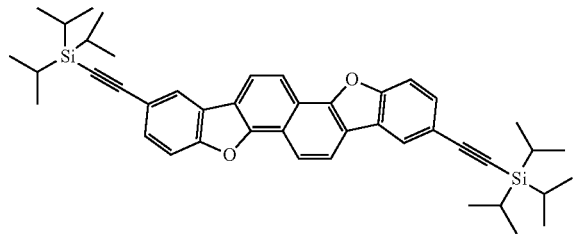

-continued
A-47
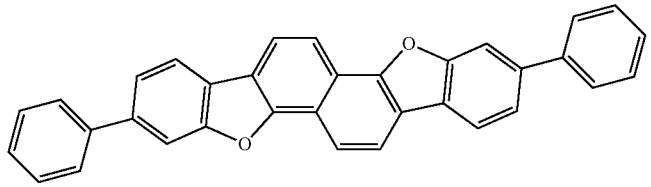
A-48
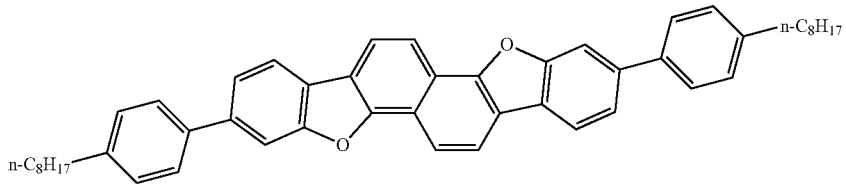
A-49
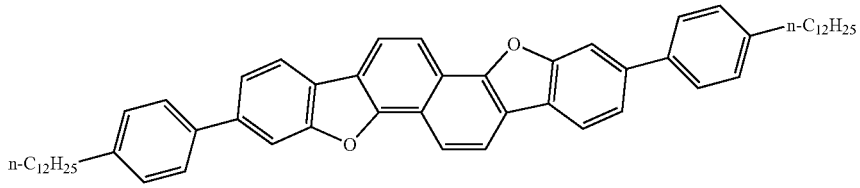
A-50
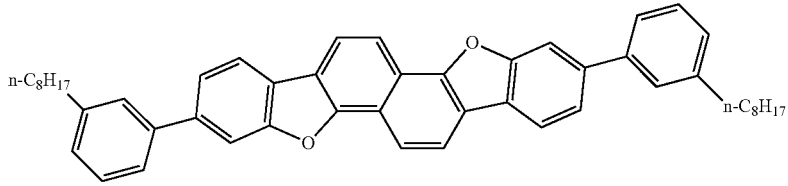
A-51
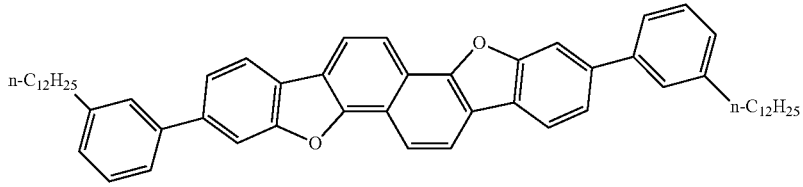
A-52
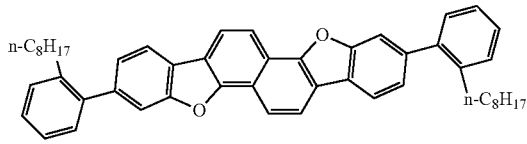
A-53
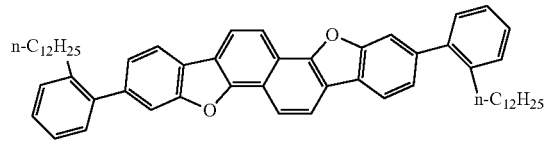
A-63
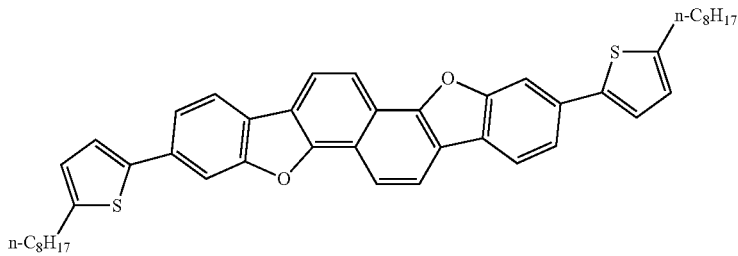
A-64
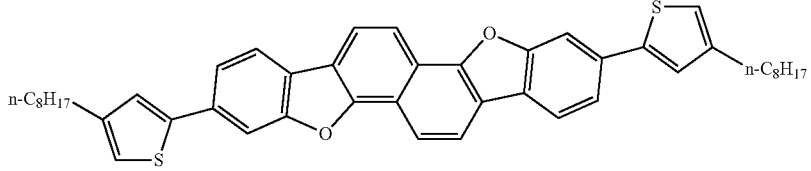

-continued
A-65
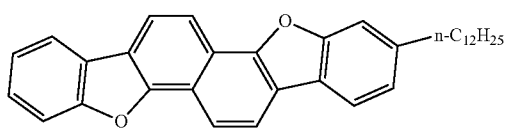
A-66
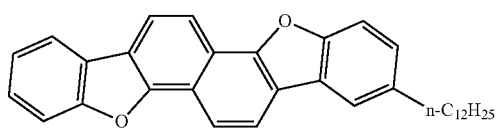
A-67
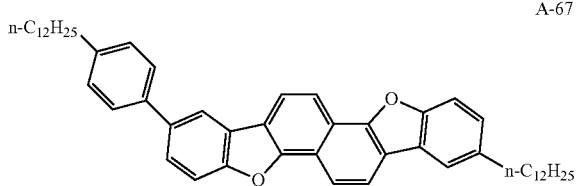
A-68
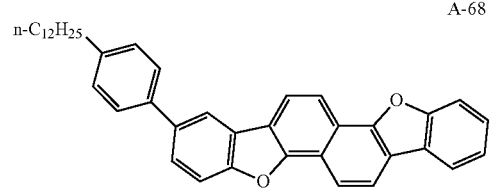
A-69
A-70
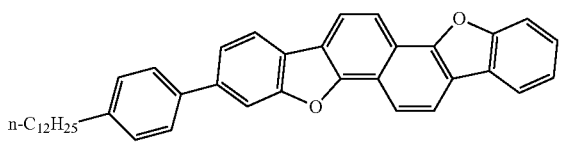
A-71
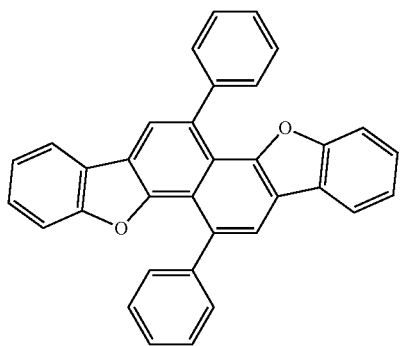
A-72
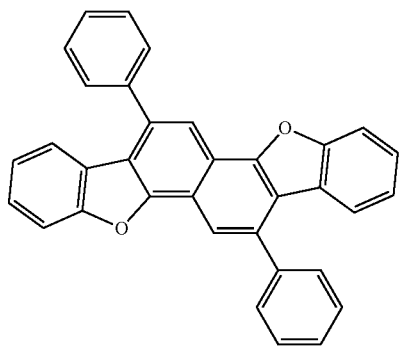
A-73
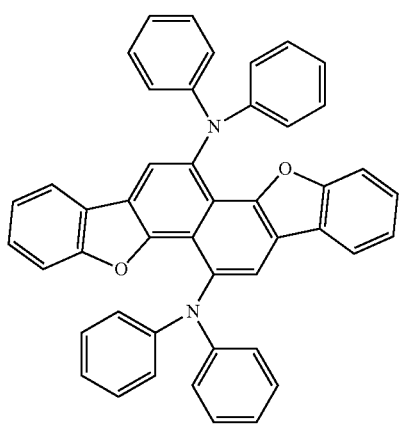
A-74
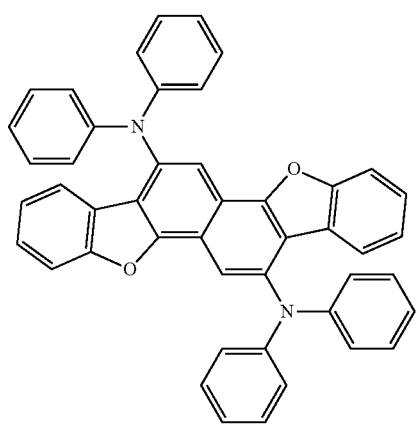

-continued
A-75
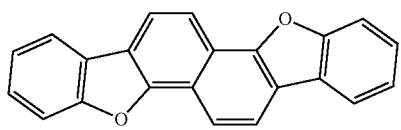
A-76
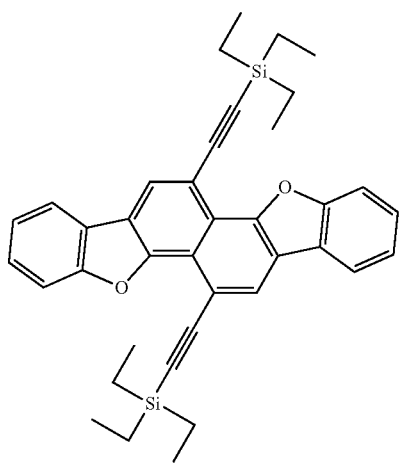
A-77
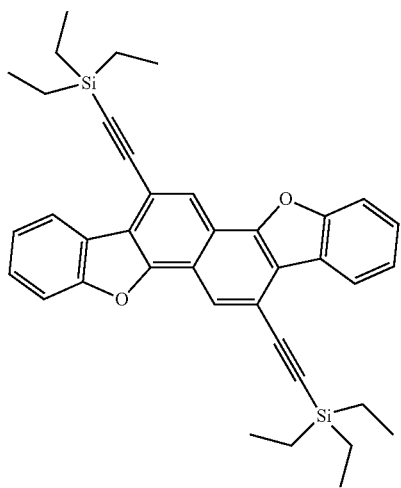
A-78
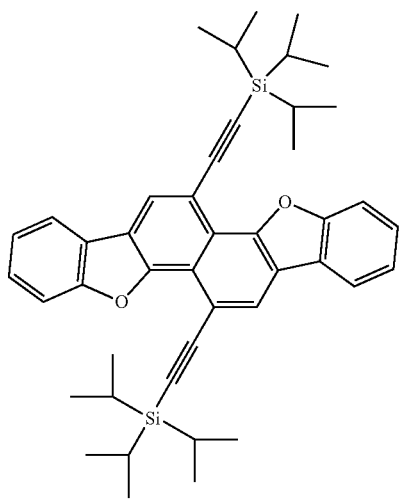
A-79
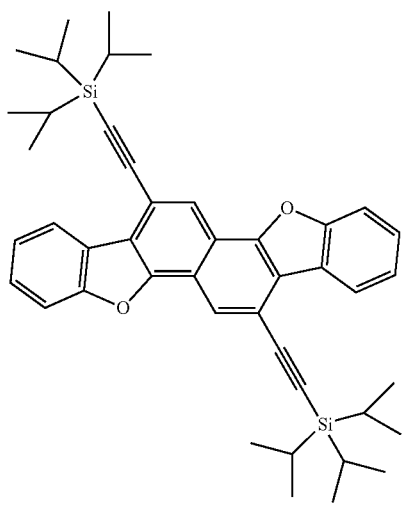

-continued
B-1
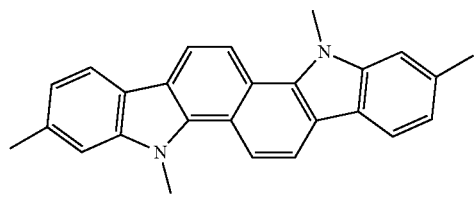
B-2
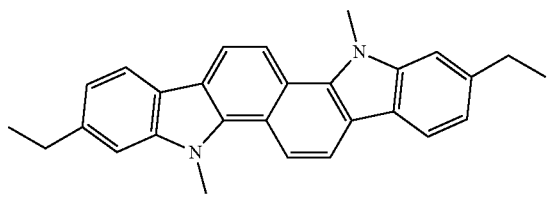
B-3
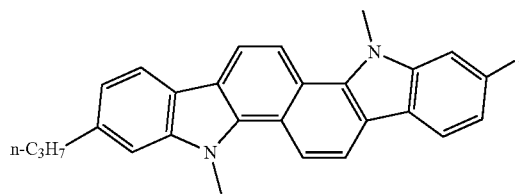
B-4
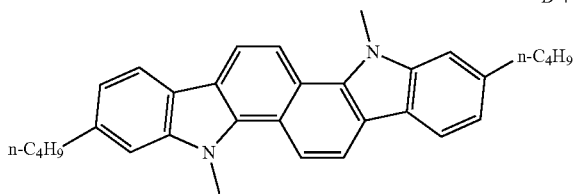
B-5
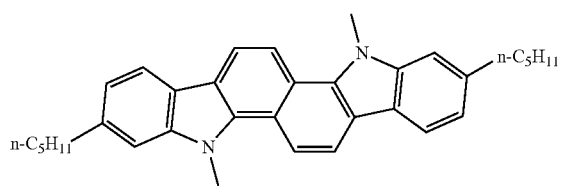
B-6
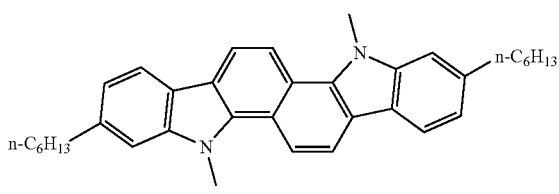
B-7
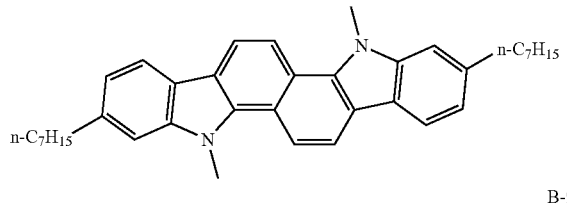
B-8
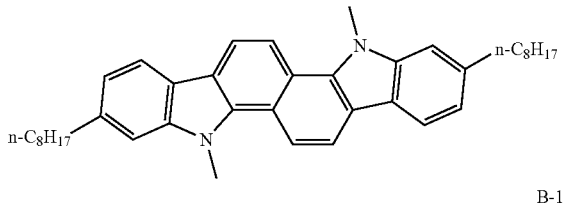
B-9
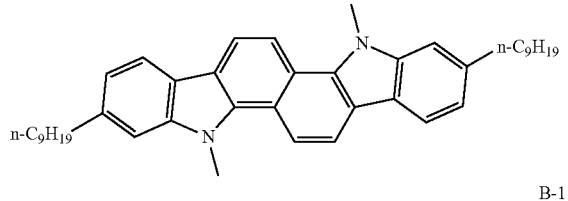
B-10
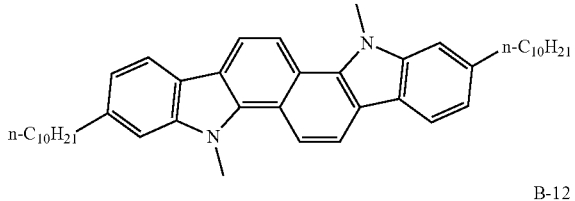
B-11
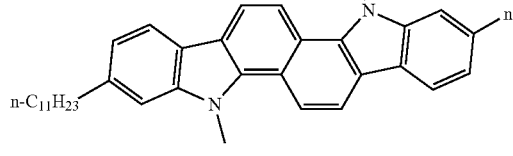
B-12
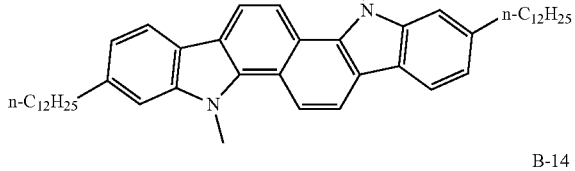
B-13
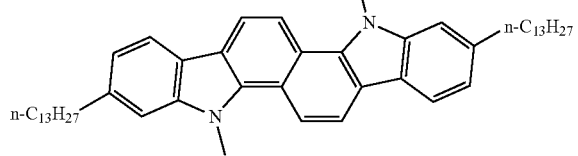
B-14
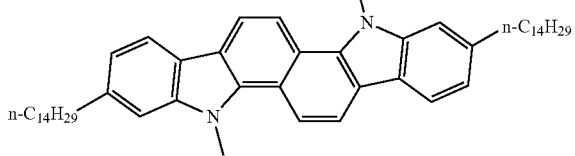
B-15
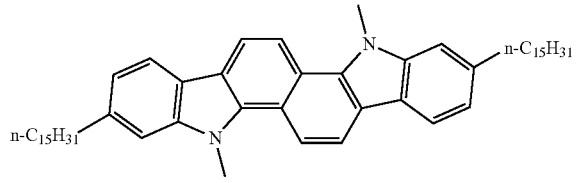
B-16
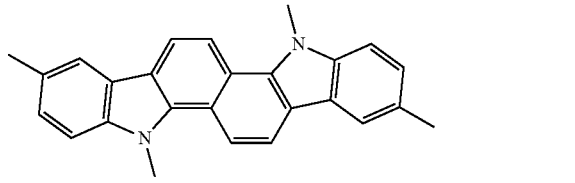

-continued
B-17
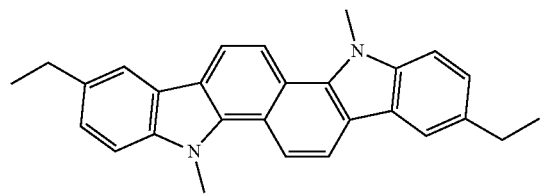
B-18
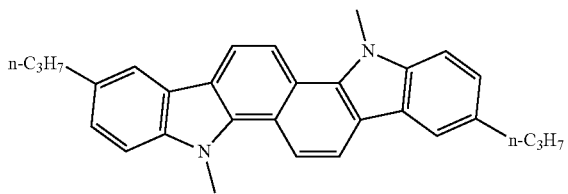
B-19
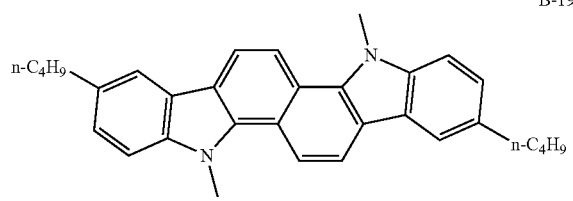
B-20
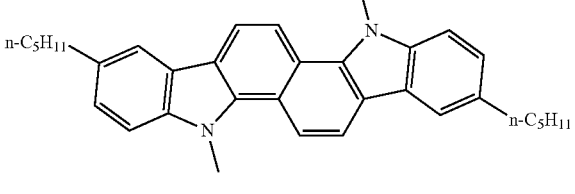
B-21
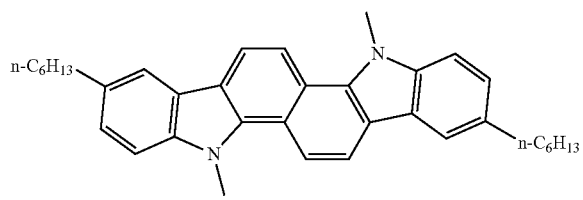
B-22
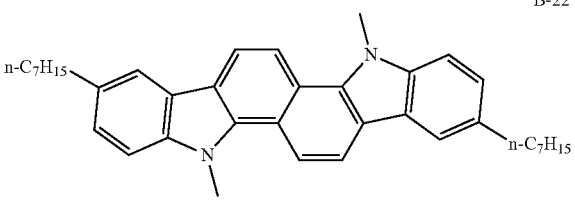
B-23
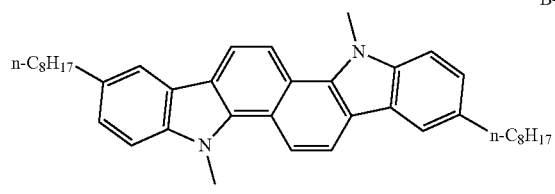
B-24
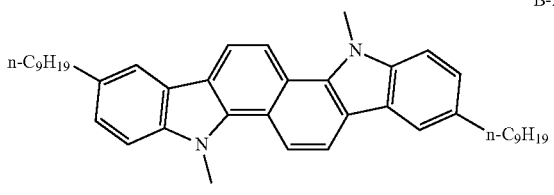
B-25
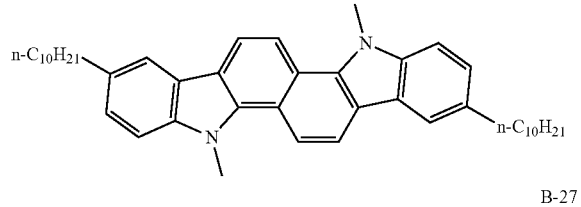
B-26
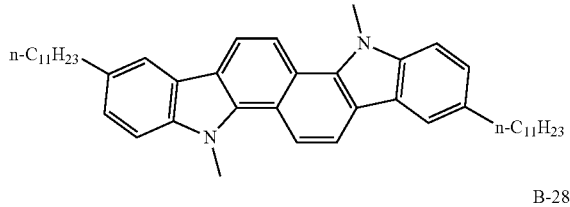
B-27
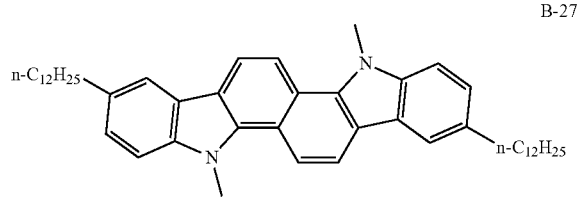
B-28
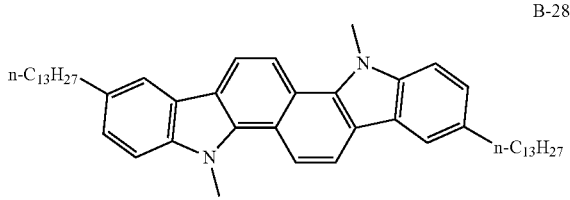
B-29
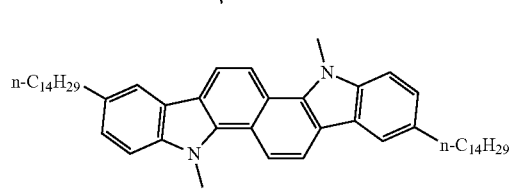
B-30
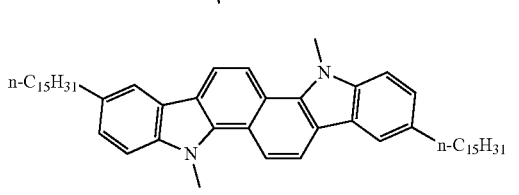
B-31
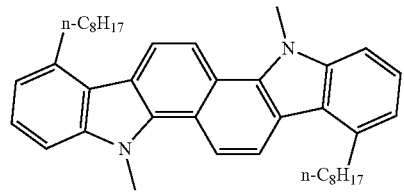
B-32
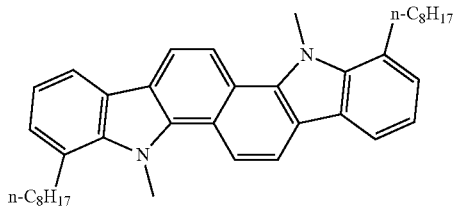

-continued
| 25 | 26 |
|---|---|
| B-33 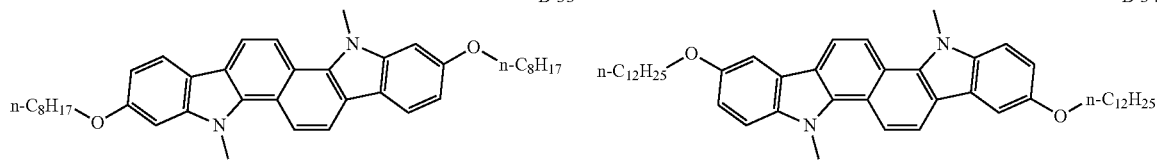 | B-34 |
| B-35 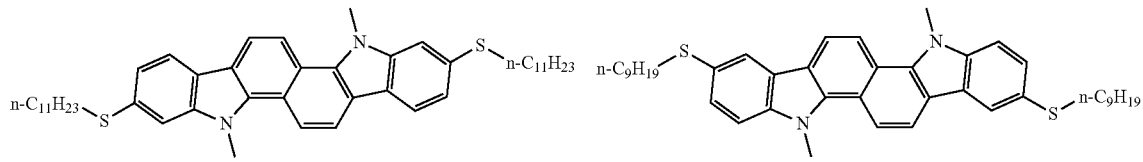 | B-36 |
| B-37 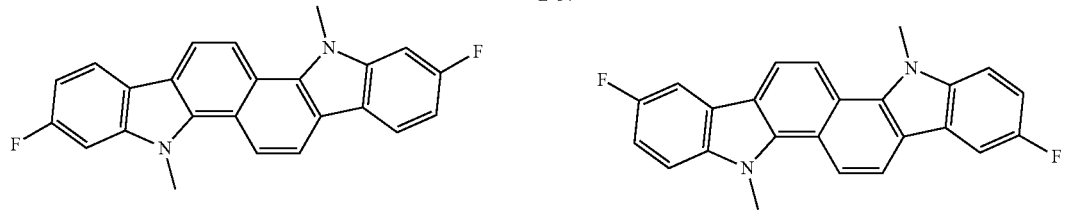 | B-38 |
| B-39 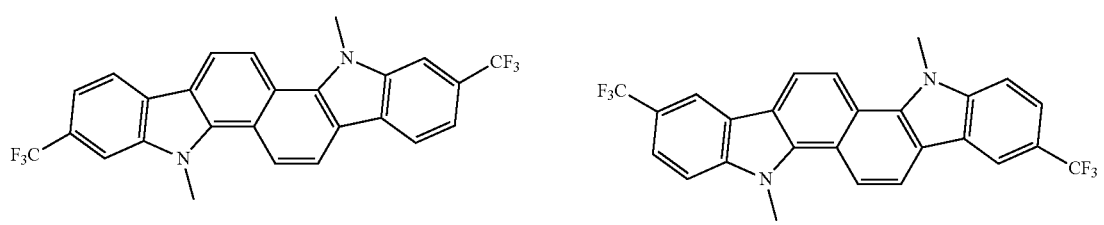 | B-40 |
| B-41 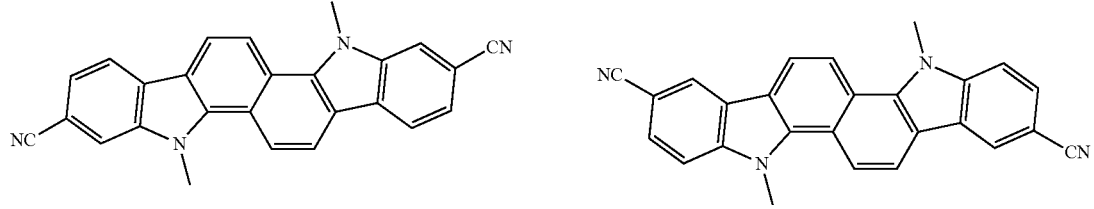 | B-42 |
| B-43 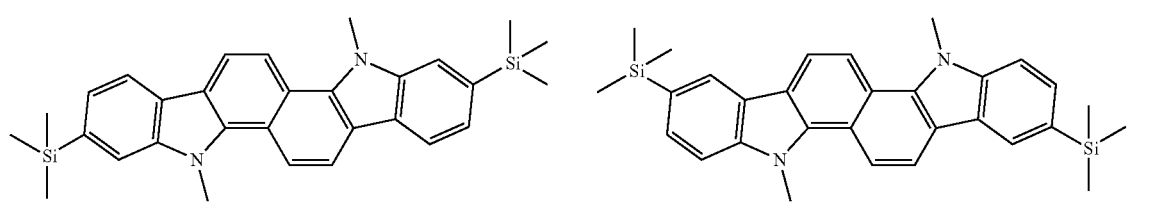 | B-44 |
| B-45 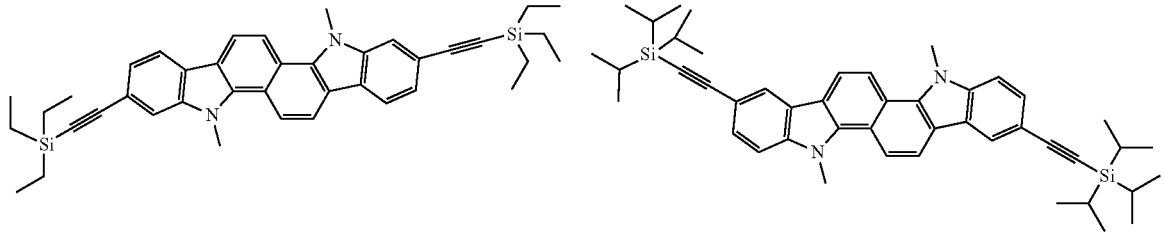 | B-46 |

-continued
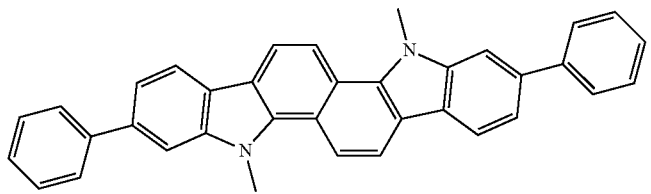
B-47
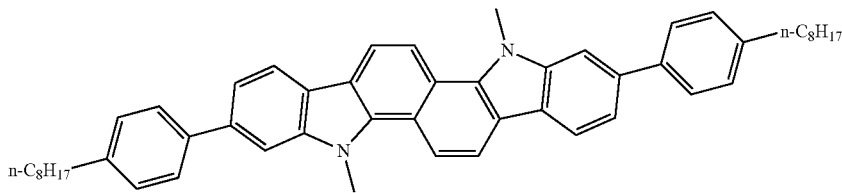
B-48
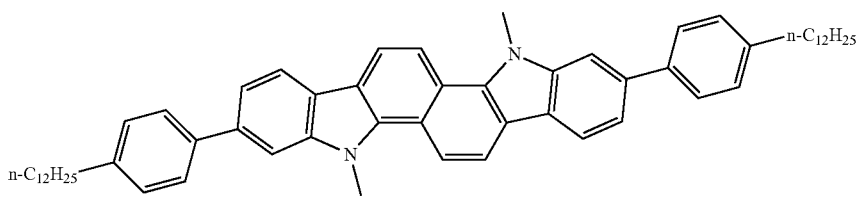
B-49
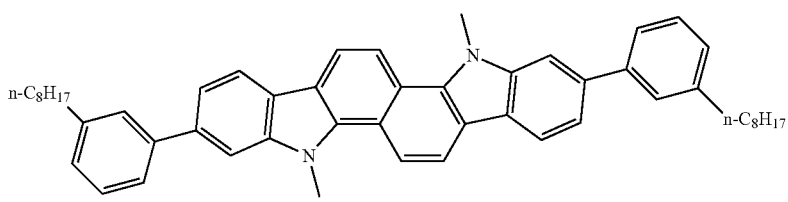
B-50
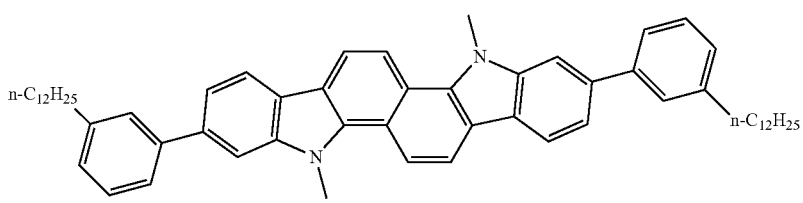
B-51
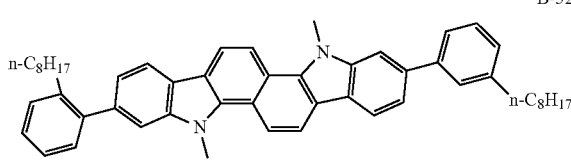
B-52
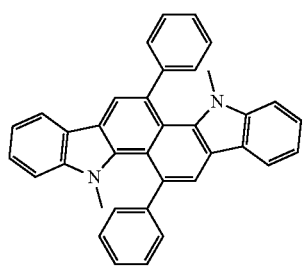
B-53

-continued
B-54
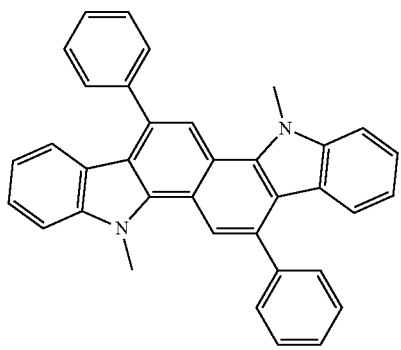
B-55
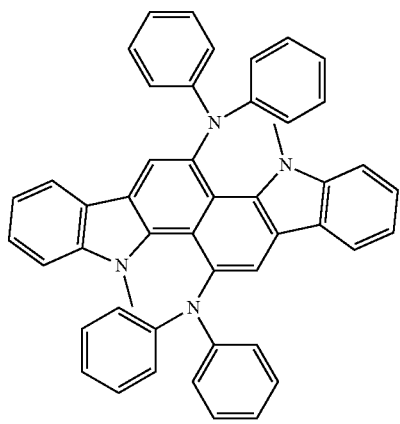
B-56
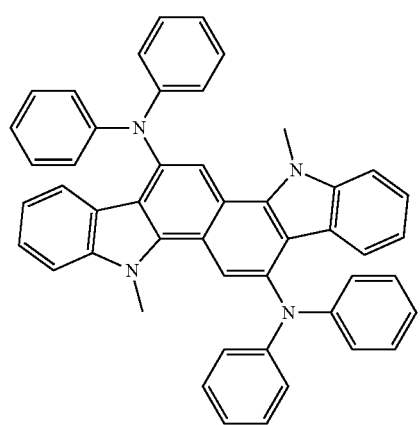
B-57
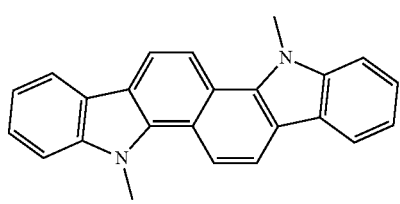
B-58
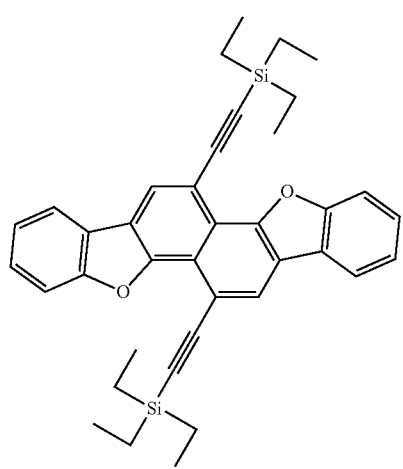
B-59
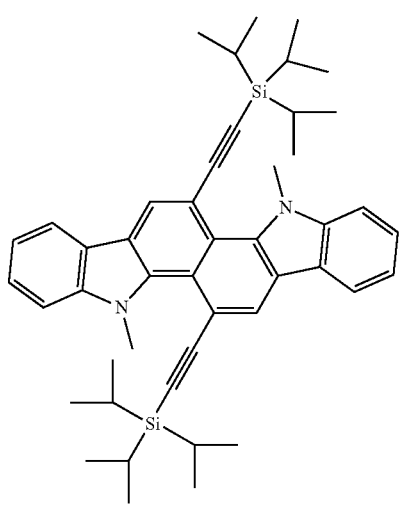

B-60

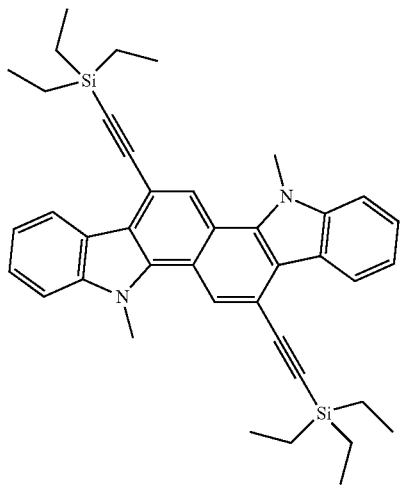

B-61

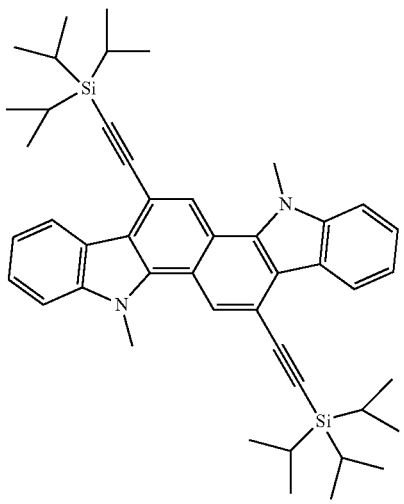

The polycyclic ring-fused compound of the invention can be synthesized by a known method; for example, the boronic acid synthesis shown by the following reaction (A), the acetyl protection reaction shown by the following formula (B), the Suzuki coupling reaction using a transitional metal shown by the following formula (C) and the annulation reaction shown by the following formula (D).

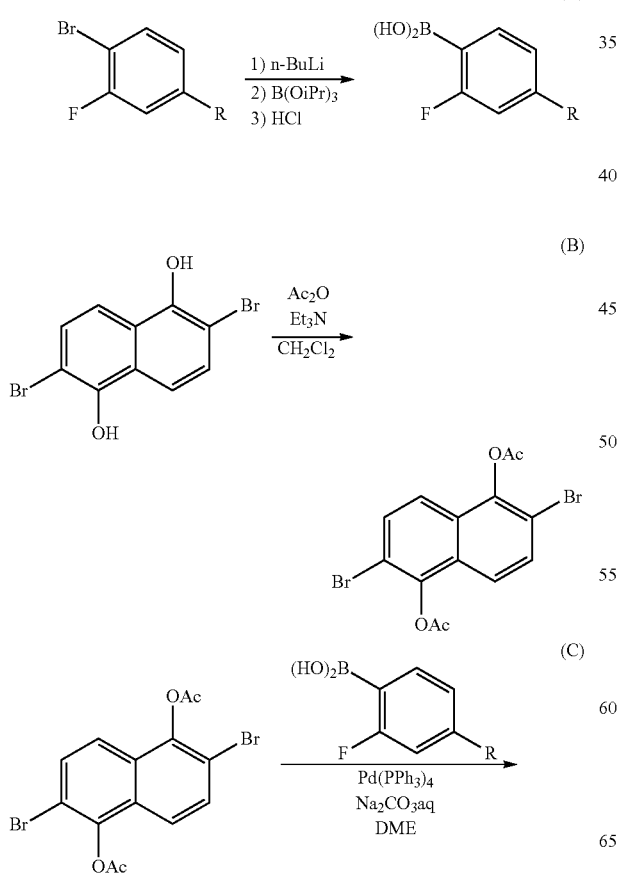

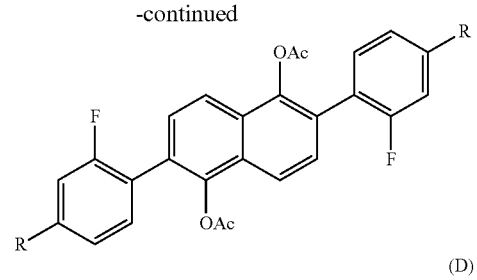

In an electric device like a transistor, the field effect mobility or the on/off ratio can be enhanced by using a material having a high purity. Therefore, according to need, it is desired that the compound be purified by techniques such as column chromatography, re-crystallization, distillation and sublimation. Preferably, by using these purification methods repeatedly or by combining some of these methods, the purity of the compound of the invention can be improved. Further, it is desired that the sublimation should be repeated at least twice or more as the final step of the purification. By using these techniques, it is preferable to allow the compound to have a purity of 90% or more. By allowing the purity to be further preferably 95% or more and particularly preferably 99% or more, the field effect mobility or the on-off ratio of an organic thin film transistor can be enhanced, and at the same time, performance intrinsic to the material can be brought out.

Next, the device configuration of the organic thin film transistor of the invention is explained below.

The organic thin film transistor of the invention has a configuration in which it comprises, on a substrate, at least three terminals of a gate electrode, a source electrode and a drain electrode, an insulator layer and an organic semiconductor layer, and current flowing between the source electrode and the drain electrode is controlled by applying a voltage to the gate electrode. It is preferred that the organic semiconductor layer contain the above-mentioned compound for an organic thin film transistor of the invention.

No specific restrictions are imposed on the structure of the transistor, and it may have a known device configuration except for the component of the organic semiconductor layer. Specific examples of the device configuration of the organic thin film transistor will be explained with reference to the drawings.

FIGS. 1 to 4 are each show one example of the device configuration of the organic thin film transistor of the invention.

In an organic thin film transistor 1 shown in FIG. 1, on a substrate 10, a source electrode 11 and a drain electrode 12 are provided which are formed such that they are opposed with a predetermined distance therebetween. Further, an organic semiconductor layer 13 is formed so as to cover the source electrode 11, the drain electrode 12 and the gap therebetween. Further, an insulator layer 14 is stacked thereon. A gate electrode 15 is formed on the insulator layer 14 and above the gap between the source electrode 11 and the drain electrode 12.

Figure 2:
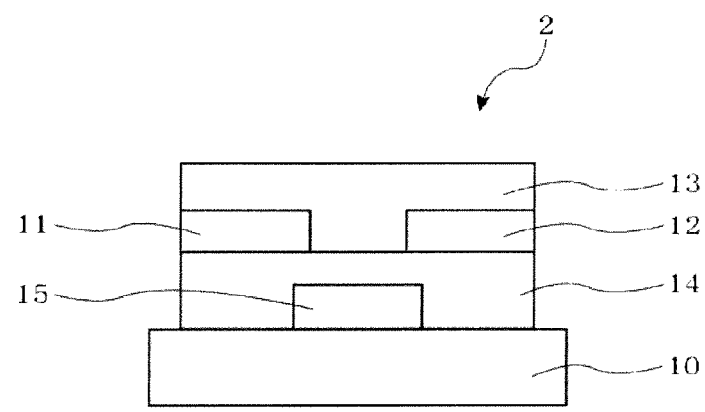
FIG. 2 is a view showing one example of the device configuration of the organic thin film transistor of the invention.

In an organic thin film transistor 2 shown in FIG. 2, on the substrate 10, the gate electrode 15 and the insulator layer 14 are provided in this sequence. On the insulator layer 14, a pair of the source electrode 11 and the drain electrode 12 is provided which are formed with a predetermined distance therebetween. The organic semiconductor layer 13 is formed thereon. The organic semiconductor layer 13 constitutes a channel region. The on-off operation is conducted by controlling current flowing between the source electrode 11 and the drain electrode 12 with a voltage applied to the gate electrode 15.

Figure 3:
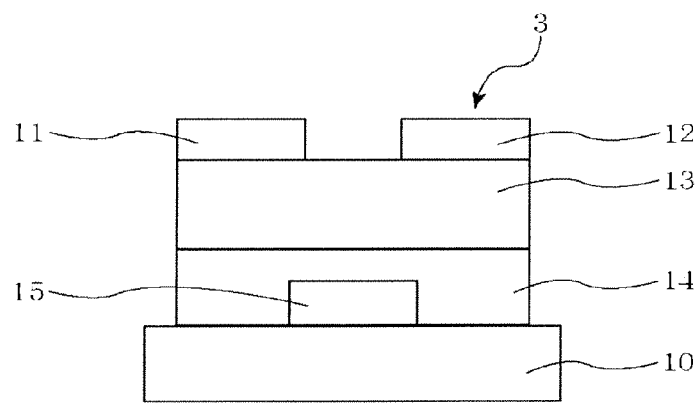
FIG. 3 is a view showing one example of the device configuration of the organic thin film transistor of the invention.

In an organic thin film transistor 3 shown in FIG. 3, on the substrate 10, the gate electrode 15, the insulator layer 14 and the organic semiconductor layer 13 are provided in this sequence. On the organic semiconductor layer 13, a pair of the source electrode 11 and the drain electrode 12 is provided which are formed with a predetermined distance therebetween.

Figure 4:
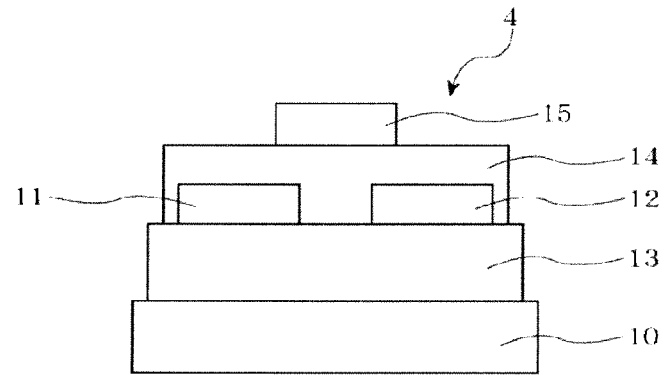
FIG. 4 is a view showing one example of the device configuration of the organic thin film transistor of the invention.

In an organic thin film transistor 4 shown in FIG. 4, on the substrate 10, the organic semiconductor layer 13 is provided. On the organic semiconductor layer 13, a pair of the source electrode 11 and the drain electrode 12 is provided which are formed with a predetermined distance therebetween. Further, the insulator layer 14 and the gate electrode 15 are provided in this sequence.

The organic thin film transistor of the invention has a field effect transistor structure (FET: Field Effect Transistor). As mentioned above, there are some configurations different in the position of the electrodes, the stacking order of the layers or the like. The organic thin film transistor has an organic semiconductor layer (organic compound layer), a source electrode and a drain electrode which are formed such that they are opposed with a predetermined distance therebetween, and a gate electrode which is formed with a predetermined distance from the source electrode and the drain electrode. Current flowing between the source electrode and the drain electrode is controlled by applying a voltage to the gate electrode. The distance between the source electrode and the drain electrode is determined according to the application in which the organic thin film transistor of the invention is used, but it is normally 0.1 μm to 1 mm, preferably 1 μm to 100 μm, and further preferably 5 μm to 100 μm.

In addition to the above-mentioned configurations, various configurations have been proposed for organic thin film transistors. The configuration of the organic thin film transistor of the invention is not restricted to the configuration as mentioned above as long as the on-off operation is conducted by controlling current flowing between the source electrode and the drain electrode with an applied voltage to the gate electrode.

Figure 5:
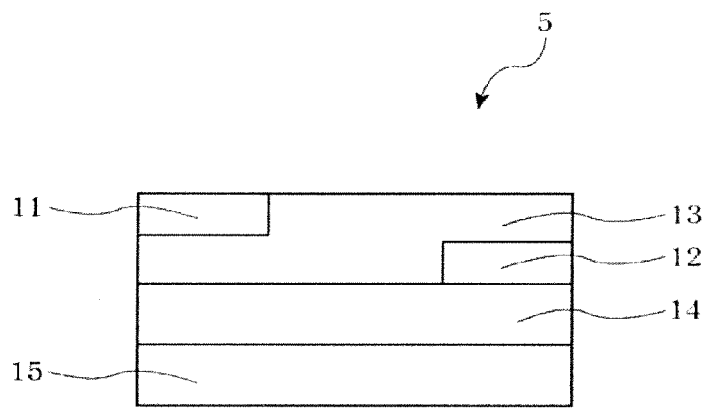
FIG. 5 is a view showing one example of the device configuration of the organic thin film transistor of the invention.
Figure 6:
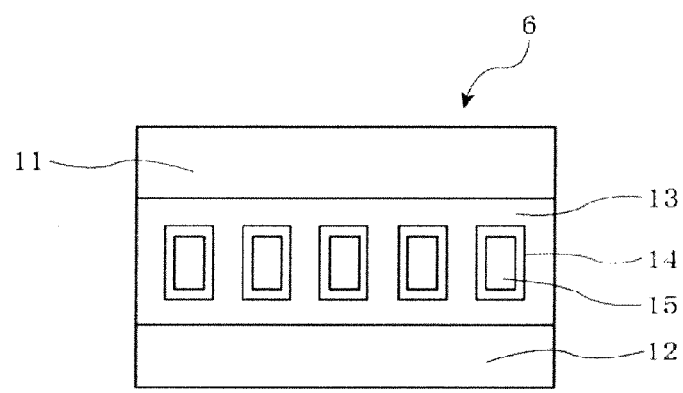
FIG. 6 is a view showing one example of the device configuration of the organic thin film transistor of the invention.

For example, it may have a device configuration like the top and bottom contact type organic thin film transistor 5 (see FIG. 5) proposed by Yoshida et al. of the National Institute of the Advanced Industrial Science and Technology in 27a-M-3 (March, 2002) of the preprints of the 49$^{th}$ Japanese Journal Applied Physics or a vertical organic thin film transistor 6 (see FIG. 6) proposed by Kudo et at of Chiba University in page 1440 of the Journals of the Institute of Electrical Engineers of Japan 118-A (1998).

Hereinbelow, each constitutional element of the organic thin film transistor is explained.
(Organic Semiconductor Layer)

The organic semiconductor layer in the organic thin film transistor of the invention comprises the compound for an organic thin film transistor of the invention. Although the film thickness of the organic semiconductor layer is not particularly restricted, it is normally 0.5 nm to 1 μm, and preferably 2 nm to 250 nm.

Further, the method for forming the organic semiconductor layer is not particularly restricted and it can be formed by a known method. For example, printing or coating method such as the molecular beam epitaxy method (the MBE method), the vacuum vapor deposition method, the chemical vapor deposition, the dipping method of a solution in which a material is dissolved in a solvent, the spin coating method, the casting method, the bar coat method, the roll coat method, and the ink-jet method, baking, electro-polymerization, molecular beam deposition, self-assembly from a solution, and combination thereof.

In the above-mentioned forming method, no specific restrictions are imposed on a solvent which is used when an organic semiconductor is formed from a solution of an organic semiconductor material in a solvent. For example, an alcohol-based solvent, a ketone-based solvent, a hydrocarbon-based solvent, a halogenated hydrocarbon-based solvent, a nitrile-based solvent and an aprotic polar solvent can be given.

Since the field effect mobility can be improved by improving the crystallinity of the organic semiconductor layer, in order to obtain a high performance device, it is preferable to be annealed after film formation irrespective of the film formation method. It is preferable to be annealed at a temperature of 50 to 200° C., further preferably 70 to 200° C. The annealing time is preferably 10 minutes to 12 hours, with 1 to 10 hours being further preferable.

In the invention, for the organic semiconductor layer, one kind of the compound shown by the formula (1) may be used, and plural kinds thereof may be combined. By using known semiconductors such as pentacene and a thiophene oligomer, it may be formed to a thin film in which plural materials are mixed, and plural layers formed of different materials may be stacked.

(Substrate)

The substrate in the organic thin film transistor of the invention has a function of supporting the structure of the organic thin film transistor. As the material for the substrate, in addition to glass, inorganic compounds such as metal oxides or nitrides, plastic films (PET, PES, PC) or a metal substrate or a composite or a stacked body of these or the like can be used. Further, if the structure of the organic thin film transistor can be fully supported by other constitutional elements than the substrate, the substrate may not be used. As the material for the substrate, silicon (Si) wafer may frequently be used. However, it is possible to use Si itself as the substrate which also functions as the gate electrode. Further, it is possible to oxidize the surface of Si to form $SiO_2$ to use it as an insulating layer. In this case, a layer of a metal such as Au may be formed on the Si substrate which also functions as the gate electrode as the electrode for connecting a lead wire.

(Electrode)

No specific restrictions are imposed on the material for the gate electrode, the source electrode and the drain electrode in the organic thin film transistor of the invention as long as they are conductive materials. Platinum, gold, silver, nickel, chromium, copper, iron, tin, antimony, lead, tantalum, indium, palladium, tellurium, rhenium, iridium, aluminum, ruthenium, germanium, molybdenum, tungsten, tin oxide antimony, indium tin oxide (ITO), fluoride-doped zinc oxide, zinc, carbon, graphite, glassy carbon, silver paste and carbon paste, lithium, beryllium, sodium, magnesium, potassium, calcium, scandium, titanium, manganese, zirconium, gallium, niobium, sodium potassium alloy, a magnesium/copper mixture, a magnesium/silver mixture, a magnesium/aluminum mixture, a magnesium/indium mixture, an aluminum/aluminum oxide mixture, a lithium/aluminum mixture, or the like can be used.

As the method for forming the electrode, deposition, electron beam deposition, sputtering, the atmospheric plasma method, ion plating, chemical vapor deposition, electrodeposition, electroless plating, spin coating, printing or ink-jetting or the like can be given. Further, as the method of patterning which is conducted according to need, a method in which a conductive thin film formed by the above-mentioned method is formed into electrodes by a known photolithographic method or a lift-off method, a method in which the conductive thin film formed by the above-mentioned method is heat-transferred to metal foil such as aluminum or copper, and then a resist is formed by the ink-jet method or the like, followed by etching.

The film thickness of the thus formed electrode is not particularly restricted as long as it passes electric current. The film thickness is preferably 0.2 nm to 10 µm, further preferably 4 nm to 300 nm. As long as the thickness of the electrode is within this range, a drop in voltage does is not caused by an increase in resistance due to a small film thickness. In the above-mentioned film thickness range, since it is not too large, film formation does not take time, and hence, stacking of layers can be conducted smoothly without causing steps when a protective layer, an organic semiconductor layer or other layers are stacked.

In the organic thin film transistor of the invention, as the other method for forming the source electrode, the drain electrode and the gate electrode, it is possible to form by using a fluidic electrode material such as a solution, a paste, ink, a dispersion liquid or the like, each containing the above-mentioned conductive material. In this case, in particular, a method in which a fluidic electrode material containing a conductive polymer or metal fine particles containing platinum, gold, silver or copper is used is preferable. As the solvent or the dispersion medium, in order to suppress damage on an organic semiconductor, a solvent or a dispersion medium containing 60 mass % or more, preferably 90 mass % or more of water is preferable. As the dispersion containing metal fine particles, a known conductive paste or the like can be used, for example. Normally, a dispersion containing metal fine particles having a particle size of 0.5 nm to 50 nm or 1 nm to 10 nm is preferable. As the material for metal fine particles, platinum, gold, silver, nickel, chromium, copper, iron, tin, antimony, lead, tantalum, indium, palladium, tellurium, rhenium, iridium, aluminum, ruthenium, germanium, molybdenum, tungsten, zinc, or the like can be used. It is preferable to form electrodes using a dispersion in which these metal fine particles are dispersed in a dispersion medium such as water or an arbitral organic solvent by using a dispersion stabilizer formed mainly of an organic material. As the method for producing such a dispersion of metal fine particles, a physical forming method such as the gas evaporation method, the sputtering method and the metal vapor synthesis method or a chemical forming method such as the colloidal method and the co-precipitation method, in which metal ions are reduced in a liquid phase to form metal fine particles. Preferably, a dispersion of metal fine particles produced by the colloidal method disclosed in JP-A-H11-76800, JP-A-H11-80647, JP-A-H11-319538 and JP-A-2000-239853 or the gas evaporation method disclosed in JP-A-2001-254185, JP-A-2001-53028, JP-A-2001-35255, JP-A-2000-124157 and JP-A-2000-123634.

The electrode may be formed by directly performing patterning according to the ink-jet method by using the above-mentioned dispersion containing fine metal particles, or may be formed from a coating film by lithography, laser ablation or the like. Further, it is possible to use a method for patterning according to the printing method such as relief printing, intaglio printing, planographic printing or screen printing. The electrode is shaped, and the solvent is dried. Thereafter, according to need, the electrode is heated along with the shape thereof at a temperature of 100° C. to 300° C., preferably 150° C. to 200° C., whereby fine metal particles are thermally bonded, thus making it possible to form an electrode pattern having an intended shape.

As other materials for the gate electrode, the source electrode and the drain electrode, it is also preferable to use known conductive polymers of which the conductivity is improved by doping or the like as the material. For example, a complex of conductive polyaniline, conductive polypyrrole, conductive polythiophene, poly(ethylenedioxy)thiophene (PEDOT) doped with polystyrene sulfonic acid can be preferably used. These materials can reduce contact resistance between the source electrode and the drain electrode, and the organic semiconductor layer. To form the electrode, patterning may be performed according to the inkjet method, and the electrode may be formed from the coating film by lithography, laser ablation, or the like. Further, it is possible to use a method for patterning according to the printing method such as relief printing, intaglio printing, planographic printing or screen printing.

In particular, as the material for forming the source electrode and the drain electrode, of the above-mentioned materials, materials having a low electric resistance in a surface being in contact with the organic semiconductor layer, are preferable. That is, this electric resistance corresponds to a field effect mobility when an electric-current control device is manufactured, and, in order to obtain a high mobility, resistance is required to be as small as possible. Generally, this depends on the magnitude relationship between the work function of electrode materials and the energy level of the organic semiconductor layer.

It is preferred that the following relationship be satisfied, in which a is the work function (W) of materials for the electrodes, b is the ionization potential (Ip) of the organic semiconductor layer, and c is the electron affinity (Af) of the organic semiconductor layer. Herein, a, b, and c are all positive values relative to the vacuum level.

In the case of a p-type organic thin film transistor, it is preferred that the relationship b−a<1.5 eV (formula (I)) be satisfied, further preferably b−a<1.0 eV. If this relationship is kept in the relationship with the organic semiconductor layer, a high-performance device can be obtained. It is preferable to select as large a work function as possible especially for the work function of the electrode materials. It is preferred that the work function of the electrode material be 4.0 eV or more, further preferably 4.2 eV or more. The value of the work function of the metal may be selected from the list of effective metals having a work function of 4.0 eV or more stated in Chemistry Manual Basic Edition II, page 493 (Revised third edition, edited by Chemical Society of Japan, issued by Maruzen Co., Ltd., 1983). Examples of such metals having a large work function include Ag (4.26, 4.52, 4.64, 4.74 eV), Al (4.06, 4.24, 4.41 eV), Au (5.1, 5.37, 5.47 eV), Be (4.98 eV), Bi (4.34 eV), Cd (4.08 eV), Co (5.0 eV), Cu (4.65 eV), Fe (4.5, 4.67, 4.81 eV), Ga (4.3 eV), Hg (4.4 eV), Ir (5.42, 5.76 eV), Mn (4.1 eV), Mo (4.53, 4.55, 4.95 eV), Nb (4.02, 4.36, 4.87 eV), Ni (5.04, 5.22, 5.35 eV), Os (5.93 eV), Pb (4.25 eV), Pt (5.64 eV), Pd (5.55 eV), Re (4.72 eV), Ru (4.71 eV), Sb (4.55, 4.7 eV), Sn (4.42 eV), Ta (4.0, 4.15, 4.8 eV), Ti (4.33 eV), V (4.3 eV), W (4.47, 4.63, 5.25 eV) and Zr (4.05 eV).

Of these, noble metals (Ag, Au, Cu, Pt), and Ni, Co, Os, Fe, Ga, Ir, Mn, Mo, Pd, Re, Ru, V and W are preferable. In addition to metals, ITO, conductive polymers such as polyaniline and PEDOT:PSS and carbon are preferable. No particular restrictions are imposed on the electrode materials as long as the work function satisfies the formula (I) even if the material contains one or more kinds of the above-mentioned substances having a large work function.

In the case of an n-type organic thin film transistor, it is preferred that the relationship a−c<1.5 eV (formula (II)) be satisfied, further preferably a−c<1.0 eV. If this relationship is kept in the relationship with the organic semiconductor layer, a high-performance device can be obtained. It is preferable to select as small a work function as possible especially for the work function of the electrode material. It is preferable to select a work function of the electrode material of 4.3 eV or less, further preferably 3.7 eV or less.

As for the specific examples of such metals having a small work function, selection may be made from the list of effective metals having a work function of 4.3 eV or less described in Chemistry Manual Basic Edition II, page 493 (Revised third edition, edited by Chemical Society of Japan, issued by Maruzen Co., Ltd., 1983). Specific examples include Ag (4.26 eV), Al (4.06, 4.28 eV), Ba (2.52 eV), Ca (2.9 eV), Ce (2.9 eV), Cs (1.95 eV), Er (2.97 eV), Eu (2.5 eV), Gd (3.1 eV), Hf (3.9 eV), In (4.09 eV), K (2.28 eV), La (3.5 eV), Li (2.93 eV), Mg (3.66 eV), Na (2.36 eV), Nd (3.2 eV), Rb (4.25 eV), Sc (3.5 eV), Sm (2.7 eV), Ta (4.0, 4.15 eV), Y (3.1 eV), Yb (2.6 eV), and Zn (3.63 eV). Among these metals, preferred metals are Ba, Ca, Cs, Er, Eu, Gd, Hf, K, La, Li, Mg, Na, Nd, Rb, Y, Yb, and Zn. No particular restrictions are imposed on the electrode material as long as the work function thereof satisfies the formula (II) even if the material contains one or a plurality of the above-mentioned substances having a small work function. However, metals having a small work function easily deteriorate when they are brought into contact with moisture or oxygen in the atmosphere, and hence, it is preferable to coat these small-work-function metals with metals, such as Ag or Au, which are stable in the air, if necessary. The film thickness necessary for coating is 10 nm or more, and metals can be more surely protected from oxygen and water in proportion to an increase in film thickness. However, in practical use, it is preferable to set the film thickness to be 1 pm or less from the viewpoint of productivity enhancement or the like.

In the organic thin film transistor according to the invention, a buffer layer may be provided between the organic semiconductor layer and the source and drain electrodes in order to improve injection efficiency, for example. As the buffer layer, for an n-type organic thin film transistor, compounds having an alkaline metal, or alkaline earth metal salts such as LiF, Li$_2$O, CsF, Na$_2$CO$_3$, KCl, MgF$_2$, or CaCO$_3$ used for a cathode of an organic EL device are preferable. In addition, a compound, such as Alq, which is used as an electron-injecting layer or as an electron-transporting layer in an organic EL device may be inserted as the buffer layer.

For a p-type organic thin film transistor, it is desirable to use FeCl$_3$, a cyano compound such as TCNQ, F$_4$-TCNQ and HAT, CFx, metal oxides other than oxides of alkaline metals and alkaline earth metals such as GeO$_2$, SiO$_2$, MoO$_3$, V$_2$O$_5$, VO$_2$, V$_2$O$_3$, MnO, Mn$_3$O$_4$, ZrO$_2$, WO$_3$, TiO$_2$, In$_2$O$_3$, ZnO, NiO, HfO$_2$, Ta$_2$O$_5$, ReO$_3$, and PbO$_2$, or an inorganic compound such as ZnS or ZnSe. In many cases, these oxides cause oxygen deficiency, and hence are suitable for hole injection. Further, this buffer layer may be made of an amine-based compound, such as TPD or NPD, or a compound, such as CuPc, which is used as a hole-injecting layer or as a hole-transporting layer in an organic EL device. Further, two or more of the above-mentioned compounds may preferably be used in combination.

It has been known that the buffer layer has an effect to reduce the threshold voltage by decreasing the injection barrier of carriers, and to drive the transistor with a low voltage. The reason therefor is as follows: There is a carrier trap at the interface of the organic semiconductor and the insulating layer. When a gate voltage is applied, injection of carriers occurs. The carriers injected at the beginning are used to fill up the trap. However, when the buffer layer is provided, the trap is filled up under a low voltage so that the mobility is increased. The buffer layer may be provided between the electrode and the organic semiconductor layer with a small thickness, and the thickness is 0.1 nm to 30 nm and preferably 0.3 nm to 20 nm.

(Insulator Layer)

No particular restrictions are imposed on materials used for an insulator layer in the organic thin film transistor of the invention as long as these materials have electric insulating properties and can be formed as thin films. It is possible to use materials, such as metallic oxides (including oxides of silicon), metal nitrides (including nitrides of silicon), polymers, or organic small molecules, whose electrical resistivity is 10 Ωcm or more at room temperature. Especially, an inorganic oxide film having a high relative dielectric constant is preferable.

Examples of inorganic oxides include silicon oxide, aluminum oxide, tantalum oxide, titanium oxide, tin oxide, vanadium oxide, barium strontium titanate, barium zirconate titanate, lead zirconate titanate, lead lanthanum titanate, strontium titanate, barium titanate, lanthanum oxide, fluorine oxide, magnesium oxide, bismuth oxide, bismuth titanate, niobium oxide, strontium bismuth titanate, strontium bismuth tantalate, tantalum pentoxide, bismuth tantalate niobate, trioxide yttrium, and combinations of these compounds. Silicon oxide, aluminum oxide, tantalum oxide and titanium oxide are preferable.

Further, inorganic nitrides, such as silicon nitride ($Si_3N_4$, SixNy (x, y>0)) and aluminum nitride, can be preferably used.

The insulator layer may be made of a precursor containing a metal alkoxide. In this case, for example, the substrate is covered with a solution of the precursor, and is subjected to a chemical solution process including a heat treatment, and, as a result, an insulator layer is formed.

The metals forming the metal alkoxide are selected from transition metals, lanthanoids or main group elements. Specific examples of such metals include barium (Ba), strontium (Sr), titanium (Ti), bismuth (Bi), tantalum (Ta), zirconium (Zr), iron (Fe), nickel (Ni), manganese (Mn), lead (Pb), lanthanum (La), lithium (Li), sodium (Na), potassium (K), rubidium (Rb), cesium (Cs), francium (Fr), beryllium (Be), magnesium (Mg), calcium (Ca), niobium (Nb), thallium (Tl), mercury (Hg), copper (Cu), cobalt (Co), rhodium (Rh), scandium (Sc) and yttrium (Y). Examples of alkoxides forming the metal alkoxide include those derived from alcohols including methanol, ethanol, propanol, isopropanol, butanol and isobutanol, and those derived from alkoxy alcohols including methoxyethanol, ethoxyethanol, propoxyethanol, butoxyethanol, pentoxyethanol, heptoxyethanol, methoxypropanol, ethoxypropanol, propoxypropanol, butoxypropanol, pentoxypropanol and heptoxypropanol In the invention, if the insulator layer is made of the above-mentioned materials, polarization tends to occur easily in the insulator layer, and the threshold voltage of transistor operation can be reduced. Of the above-mentioned materials, if an insulator layer is formed of silicon nitrides such as $Si_3N_4$, $Si_xNy$ and $SiON_X$ (x, y>0), a void layer tends to be generated more easily, resulting in a further decrease in threshold voltage of transistor operation.

Examples of materials for the insulator layer using organic compounds include polyimide, polyamide, polyester, polyacrylate, a photo-curable resin such as a photoradical polymerization resin and a photocationic polymerization resin, a copolymer containing acrylonitrile components, polyvinylphenol, polyvinylalcohol, novolac resin and cyanoethylpullulan.

Other examples thereof include wax, polyethylene, polychloropyrene, polyethylene terephthalate, polyoxymethylene, polyvinyl chloride, polyvinylidene fluoride, polysulfone, polyimidecyanoethyl pullulan, poly(vinylphenol) (PVP), poly(methylmethacrylate) (PMMA), polycarbonate (PC), polystyrene (PS), polyolefin, polyacrylamide, poly (acrylic acid), a novolac resin, a resol resin, polyimide, polyxylylene, and an epoxy resin. In addition to these resins, polymer materials having a high dielectric constant such as pullulan can be used.

A particularly suitable organic compound material or polymer material for the insulator layer is a material having water repellency. The use of a material having such water repellency makes it possible to control interaction between the insulator layer and the organic semiconductor layer, and makes it possible to enhance the crystallinity of the organic semiconductor layer by utilizing cohesive properties intrinsic to an organic semiconductor, whereby device performance can be improved. A polyparaxylylene derivative described in Yasuda et al., Jpn. J. Appl. Phys. Vol. 42 (2003) pp. 6614-6618 or a compound described in Janos Veres et al., Chem. Mater., Vol. 16 (2004) pp. 4543-4555 can be mentioned as an example of the organic compound.

When the top gate structure shown in FIG. 1 and FIG. 4 is used, the use of the above-mentioned organic compound as the material for the insulator layer is an effective method, since it makes it possible to form a film while lessening damage exerted on the organic semiconductor layer.

The insulator layer may be a mixed layer in which the above-mentioned inorganic or organic compound materials are used in combination, and may be a stacked layer composed of these materials. In this case, device performance can also be controlled by mixing or stacking a material having a high dielectric constant and a material having water repellency, according to need.

Further, an anodic oxidized film, or this anodic oxidized film may be used as a part of the structure of the insulator layer. Preferably, the anodic oxidized film is subjected to a sealing process. The anodic oxidized film is formed by anodizing a metal, which can be anodized, by a known method. Aluminum or tantalum can be mentioned as a metal which can be anodized. No particular restrictions are imposed on the anodizing method, and a known method can be used. An oxidized film is formed by performing an anodizing process. Any type of solution can be used as the electrolytic solution used for the anodizing process as long as a porous oxidized film can be formed. In general, sulfuric acid, phosphoric acid, oxalic acid, chromic acid, boric acid, sulfamic acid, benzenesulfonic acid, or a mixed acid produced by combining two or more kinds of the above-mentioned acids, or salts of the above-mentioned acids are used. Anodizing process conditions cannot be absolutely specified because they variously change depending on an electrolytic solution to be used. In general, appropriate conditions are an electrolyte concentration of 1 to 80 mass %, an electrolyte temperature of 5 to 70° C., an electric current density of 0.5 to 60 A/cm², a voltage of 1 to 100 volts, and an electrolysis time of 10 seconds to 5 minutes. A preferred anodizing process is to use an aqueous solution of sulfuric acid, phosphoric acid or boric acid as the electrolytic solution and to perform the process by using direct current. Alternating current can also be used instead of direct current. Preferably, the concentration of these acids is 5 to 45 mass %, and the electrolytic process is performed for 20 to 250 seconds under the conditions of an electrolyte temperature of 20 to 50° C. and an electric current density of 0.5 to 20 A/cm².

As for the thickness of the insulator layer, if the thickness is small, an effective voltage to be applied to the organic semiconductor will be increased, and hence, the driving voltage and threshold voltage of the device itself can be lowered. However, since current leakage between the source electrode and the gate electrode is increased if the thickness is small, an appropriate film thickness is required to be selected. Normally, the thickness of the insulator layer is 10 nm to 5 μm, and, preferably 50 nm to 2 μm, and more preferably 100 nm to 1 μm.

An arbitrary orientation process may be applied between the insulator layer and the organic semiconductor layer. A preferred example thereof is a method of applying a water-repellent process or the like to the surface of the insulator layer to reduce the interaction between the insulator layer and the organic semiconductor layer, thereby improving the crystallinity of the organic semiconductor layer. Specifically, a method in which a silane coupling agent such as hexamethyldisilazane, octadecyltrichlorosilane and trichloromethylsilazane, or a material for a self-assembled oriented film such as alkanephosphoric acid, alkanesulfonic acid and alkanecarboxylic acid is brought into contact with the surface of the insulating film in the liquid phase or the vapor phase to form a self-assembled film, followed by an appropriate dry process. A method is also preferable in which a film made of, for example, polyimide is formed on the surface of the insulating film as in case of the orientation of liquid crystals, and the surface of the film is subjected to a rubbing process.

Examples of methods employed for forming the insulator layer include dry processes, e.g., the vacuum vapor deposition method, the molecular beam epitaxial growth method, the ion cluster beam method, the low energy ion beam method, the ion plating method, the CVD method, the sputtering method and the atmospheric-pressure plasma method disclosed in JP-A-H11-61406, JP-A-H11-133205, JP-A-2000-121804, JP-A-2000-147209 and JP-A-2000-185362, and wet processes, e.g., the coating method, such as the spray coating method, the spin coating method, the blade coating method, the dip coating method, the casting method, the roll coating method, the bar coating method and the die coating method, and the patterning method such as printing and inkjetting. An adequate process may be used in accordance with materials. For example, as for the wet process, a method of applying and drying a liquid obtained by dispersing fine particles of an inorganic oxide into an arbitrary organic solvent or water by using a dispersion assisting agent, such as a surfactant, as necessary, or the so-called sol-gel method in which an oxide precursor, for example, an alkoxide solution, is applied and dried, are used.

No particular restrictions are imposed on the method for forming the organic thin film transistor of the invention, and a known method can be used. It is preferred that a series of device forming steps consisting of substrate mounting, gate electrode formation, insulator layer formation, organic semiconductor layer formation, source electrode formation, and drain electrode formation be carried out while completely avoiding contact with the atmosphere according to a desired device structure, because device performance can be prevented from being impaired by moisture or oxygen in the atmosphere as a result of contact with the atmosphere. Even when the device must be formed by being unavoidably brought into contact with the atmosphere once, steps subsequent to the step of organic semiconductor layer formation are performed while completely avoiding contact with the atmosphere, and, immediately before the step of organic semiconductor layer formation, a surface (in the case of an organic thin film transistor 2 shown in FIG. 2, a surface on which a source electrode and a drain electrode are partially stacked on the insulator layer, for example) on which the organic semiconductor layer is stacked is purified and activated by, for example, ultraviolet light irradiation, ultraviolet light/ozone irradiation, oxygen plasma, argon plasma or the like, and then the organic semiconductor layer is stacked thereon. Some of the materials for a p-type organic thin film transistor can improve the performance thereof by being brought into contact with the atmosphere once so as to absorb oxygen and other gases. Accordingly, contact with the atmosphere is conducted appropriately depending on materials to be used.

Further, a gas barrier layer may be formed on the entire or part of the outer peripheral surface of the organic transistor device, for example, taking into consideration an influence exerted on the organic semiconductor layer by oxygen or water contained in the atmosphere. Materials normally used in this field can be used for forming the gas barrier layer. Examples of such materials include polyvinyl alcohol, an ethylene-vinyl alcohol copolymer, polyvinyl chloride, polyvinylidene chloride and polychlorotrifluoroethylene. Further, inorganic substances having insulation properties exemplified regarding the above-mentioned insulator layer can also be used.

In the invention, it is possible to provide an organic thin film light-emitting transistor which can emit light by using current flowing between the source electrode and the drain electrode, and of which light emission is controlled by applying a voltage to the gate electrode. That is, the organic thin film transistor can be used as a light-emitting device (organic EL device). Since the transistor for controlling light emission and the light-emitting device can be integrated, cost can be reduced by increasing the aperture ratio of a display and by simplifying the manufacturing process, and as a result, a practically great advantage can be brought about. When the organic thin film transistor is used as an organic light-emitting transistor, holes are required to be injected from one of the source electrode and the drain electrode whereas electrons are required to be injected from the remaining electrode, and it is preferred that the following conditions be satisfied to improve light-emission performance.

In order to improve hole-injecting properties, in the organic thin film light-emitting transistor it is preferred that at least one of the source electrode and the drain electrode serve as a hole-injecting electrode. The hole-injecting electrode means an electrode containing a material having a work function of 4.2 eV or more as mentioned above.

In order to improve electron-injection properties, in the organic thin film light-emitting transistor, it is preferred that at least one of the source electrode and the drain electrode be an electron-injecting electrode. The electron-injecting electrode means an electrode containing a material having a work function of 4.3 eV or less as mentioned above.

An organic thin film light-emitting transistor in which one of the electrodes is a hole-injecting electrode and the other is an electron-injecting electrode is further preferable.

In order to improve hole-injection properties, it is preferred that a hole-injecting layer be inserted between at least one of the source and drain electrodes and the organic semiconductor layer. For example, an amine-based material, which is used as a hole-injecting material or a hole-transporting material in an organic EL device, can be used in the hole-injecting layer.

In order to improve electron-injecting properties, it is preferred that an electron-injecting layer be inserted between at least one of the source electrode and the drain electrode, and the organic semiconductor layer. As in the case of the hole, an electron-injecting material used in an organic EL device can be used in the electron-injecting layer.

A further preferable is an organic thin film light-emitting transistor in which a hole-injecting layer is provided on one of the electrodes, and an electron-injecting layer be provided on the other electrode.

An apparatus using the organic thin film transistor of the invention may be an apparatus which uses the organic thin film transistor of the invention. Examples thereof include a circuit, a personal computer, a display, a mobile phone, or the like.

EXAMPLES

The invention will be described in more detail with reference to the following examples.

Example 1

Synthesis of Compound (A-8)

(1) Synthesis of Compound (a)

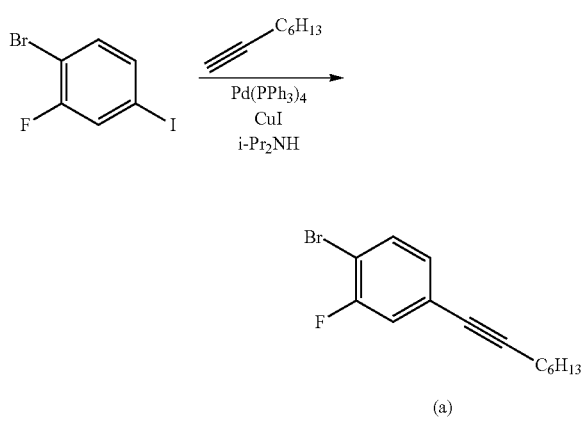

45.0 g (0.149 mol) of 1-bromo-2-fluoro-4-iodobenzene, 1.71 g (1.49 mmol) of tetrakistriphenylphosphine palladium (0), 0.56 g (2.98 mmol) of copper iodide (I) and 270 ml of diisopropylamine were placed in a flask. To the resulting mixture, 16.8 g (0.149 mol) of 1-octine and 500 ml of dehydrated toluene were added, and the reactor was stirred with heating at 40° C. for 6.5 hours. The reaction mixture was filtered, and the solvent in the filtrate was removed under reduced pressure, thereby to obtain a crude product of compound (a). This crude product was purified by column chromatography (hexane), whereby 40.1 g (yield: 95%) of compound (a) was obtained.

(2) Synthesis of Compound (b)

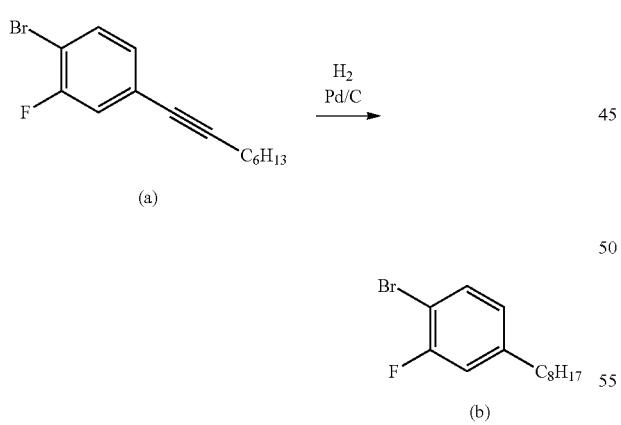

40.0 g (0.141 mol) of the compound (a), 8.0 g of palladium/carbon (Pd 5%) and 500 ml of dehydrated toluene were placed in a flask. Under atmosphere of hydrogen, the resulting mixture was stirred with heating at 60° C. for 18.5 hours. The reaction mixture was filtered, and the solvent in the filtrate was removed under reduced pressure, thereby to obtain a crude product of compound (b). This crude product was purified by column chromatography (hexane), whereby 36.4 g (yield: 90%) of compound (b) was obtained.

(3) Synthesis of Compound (c)

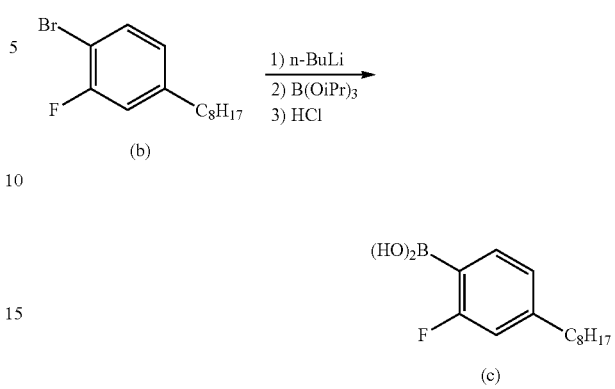

17.3 g (60.2 mmol) of the compound (b) and dehydrated tetrahydrofuran were placed in a flask, followed by cooling to −70° C. To the resulting mixture, 46.5 ml (72.2 mmol) of 1.55M-normalbutyllithium was added dropwise. The mixture was stirred at −70° C. for 1.5 hours. 22.6 g (120.0 mmol) of triisopropyl borate was added dropwise, and the temperature was elevated to room temperature, followed by stirring for 4 hours. An aqueous hydrochloric acid solution was added to the reaction mixture, and extraction was conducted with dichloromethane. The solvent in the organic phase was removed under reduced pressure, thereby to obtain a crude product of the compound (c). This crude product was purified by column chromatography (hexane: acetone), whereby 9.9 g (yield: 65%) of compound (c) was obtained.

(4) Synthesis of Compound (d)

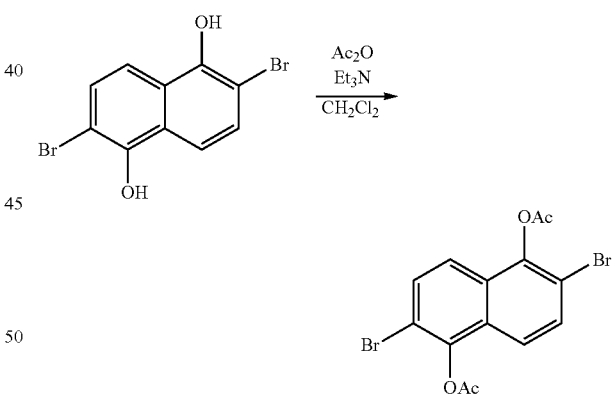

10.0 g (31 mmol) of 2,6-dibromo-1,5-dihydroxynaphthalene, 250 ml of dehydrated dichloromethane, 11.1 g (110 mmol) of triethylamine and 7.1 g (69 mmol) of acetic anhydride were placed in a flask. The resulting mixture was stirred at room temperature for 4 hours. Pure water was added to the reaction mixture, and extracted with dichloromethane. The solvent in the organic phase was removed under reduced pressure, thereby to obtain a crude product of the compound (d). This crude product was purified by column chromatography (dichloromethane), whereby 5.1 g (yield: 41%) of compound (d) was obtained.

(5) Synthesis of Compound (e)

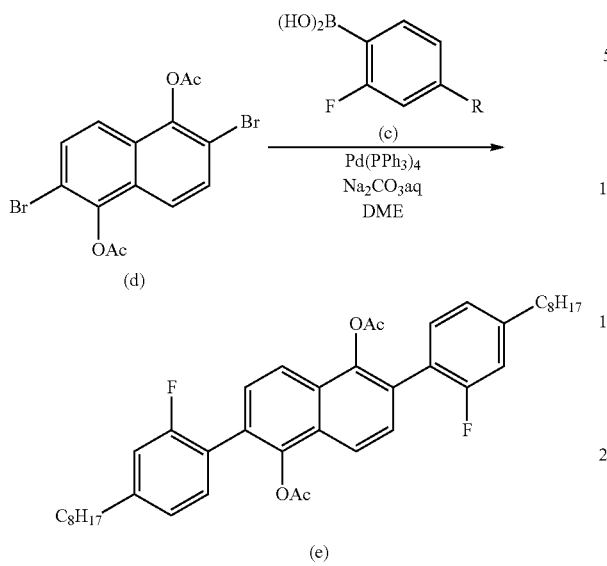

4.1 g (10.2 mmol) of compound (d), 5.7 g (22.4 mmol) of compound (c), 250 ml of dimethoxyethane, 4.3 g (40.8 mmol) of sodium carbonate, 150 ml of pure water, and 0.59 g (0.5 mmol) of tetrakis(triphenylphosphine)palladium (0) were placed in a flask. The resulting mixture was stirred at 80° C. for 3.5 hours. Pure water was added to the reaction mixture, and extracted with dichloromethane. The solvent in the organic phase was removed under reduced pressure, thereby to obtain a crude product of the compound (e). This crude product was purified by column chromatography (hexane: ethyl acetate), whereby 3.3 g (yield: 49%) of compound (e) was obtained.

(6) Synthesis of Compound (A-8)

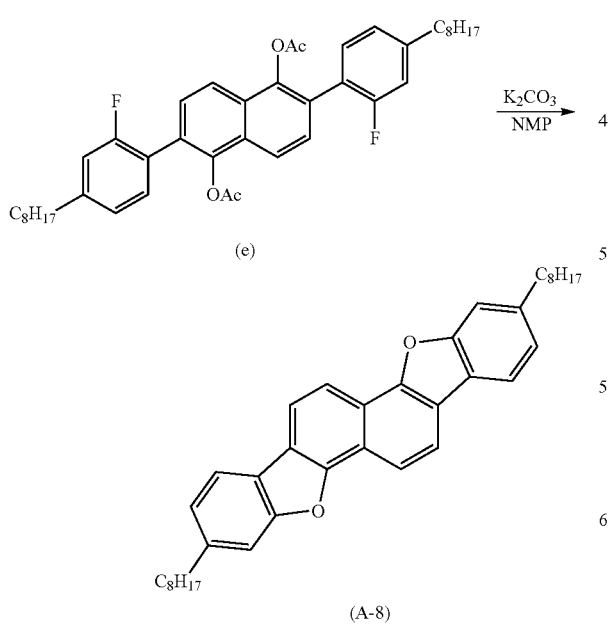

2.5 g (3.8 mmol) of the compound (e), 3.2 g (22.8 mmol) of potassium carbonate and 400 ml of dehydrated 1-methyl-2-pyrrolidone were placed. The resulting mixture was stirred with heating at 170° C. for 3 hours. The reaction mixture was cooled, and precipitated solids were filtrated and washed with pure water, thereby to obtain a crude product of compound (A-8). The resulting crude product was purified by re-crystallization and sublimation, whereby 0.95 g (yield: 47%) of compound (A-8) was obtained.

The product was identified as the intended product by the FD-MS (Field Desorption Mass Spectrometry) analysis. The measurement results of the FD-MS are shown below.

FD-MS, calcd for $C_{38}H_{44}O_2=532$, found, m/z=532 (M+, 100)

Example 2

Synthesis of Compound (A-75)

(1) Synthesis of Compound (f)

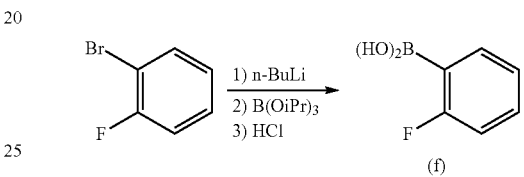

10.0 g (57.1 mmol) of 1-bromo-2-fluorobenzene and dehydrated tetrahydrofuran were placed, followed by cooling to −70° C. To the resulting mixture, 44.2 ml (68.5 mmol) of 1.55M-normalbutyllithium was added dropwise. The resulting mixture was stirred at −70° C. for 1.5 hours, and 21.5 g (114.2 mmol) of triisopropyl borate was added dropwise, and the temperature was elevated to room temperature, followed by stirring for 4 hours. An aqueous hydrochloric acid solution was added to the reaction mixture, and extracted with dichloromethane. The solvent in the organic phase was removed under reduced pressure, thereby to obtain a crude product of the compound (f). This crude product was purified by column chromatography (hexane: acetone), whereby 4.8 g (yield: 61%) of compound (f) was obtained.

(2) Synthesis of Compound (g)

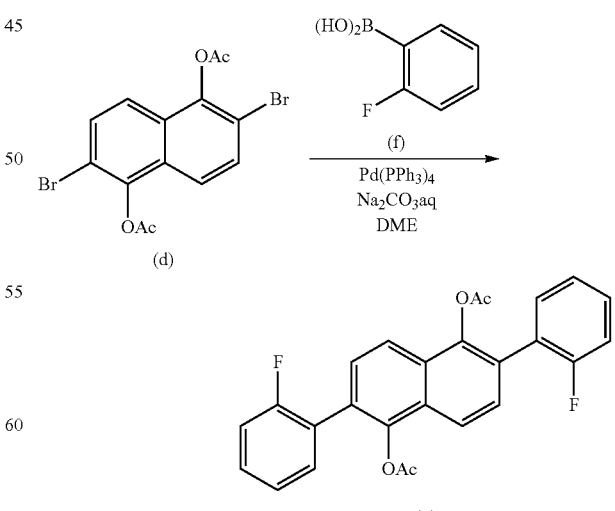

6.5 g (16.3 mmol) of the compound (d), 4.8 g (34.3 mmol) of the compound (f), 300 ml of dimethoxyethane 6.9 g (65.2 mmol) of sodium carbonate, 200 ml of pure water and 0.93 g (0.8 mmol) of tetrakis(triphenylphosphine)palladium (0) were placed in a flask. The resulting mixture was stirred with heating at 80° C. for 3.5 hours. Pure water was added to the reaction mixture, and extracted with dichloromethane. The solvent in the organic phase was removed under reduced pressure, thereby to obtain a crude product of the compound (g). This crude product was purified by column chromatography (hexane:ethyl acetate), whereby 3.8 g (yield: 54%) of compound (g) was obtained.

(2) Synthesis of Compound (A-75)

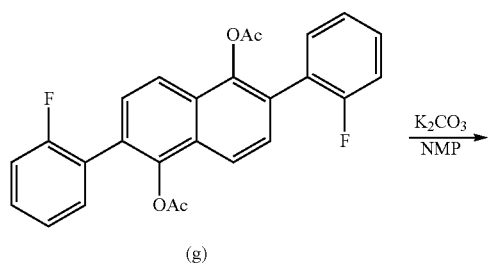

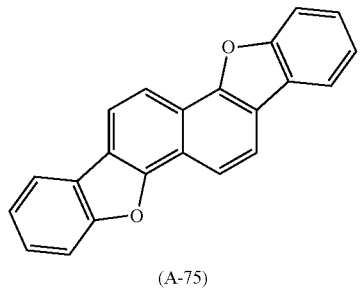

(A-75)

3.8 g (8.8 mmol) of compound (g), 7.3 g (52.8 mmol) of potassium carbonate and 800 ml of dehydrated 1-methyl-2-pyrrolidone were placed. The resulting mixture was stirred with heating at 170° C. for 3 hours. The reaction mixture was cooled, and precipitated solids were filtrated and washed with pure water, thereby to obtain a crude product of compound (A-75). The resulting crude product was purified by re-crystallization and sublimation, whereby 1.57 g (yield: 58%) of compound (A-75) was obtained.

The product was identified as the intended product by the FD-MS (Field Desorption Mass Spectrometry) analysis. The measurement results of the FD-MS are shown below.

FD-MS, calcd for $C_{22}H_{12}O_2$=308, found, m/z=308 (M+, 100)

Example 3

Synthesis of Compound (A-23)

(1) Synthesis of Compound (h)

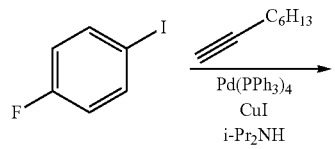

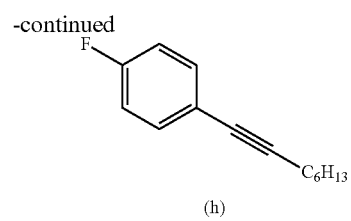

50.0 g (0.225 mol) of 1-fluoro-4-iodobenzene, 2.6 g (2.25 mmol) of tetrakis(triphenylphosphine)palladium (0), 0.85 g (4.50 mmol) of copper iodide (I) and 270 ml of diisopropylamine were placed in a flask. To the resulting mixture, 27.2 g (0.247 mol) of 1-octine and 500 ml of dehydrated toluene were added, and the reaction mixture was stirred with heating at 40° C. for 7 hours. The reaction mixture was filtered, and the solvent in the filtrate was removed under reduced pressure, thereby to obtain a crude product of compound (h). This crude product was purified by column chromatography (hexane), whereby 46.0 g (yield: 100%) of compound (h) was obtained.

(2) Synthesis of Compound (i)

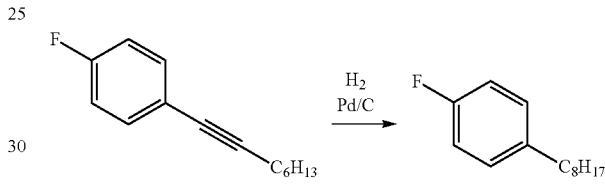

46.0 g (0.225 mol) of the compound (h), 2.3 g of palladium/carbon (Pd 5%) and dehydrated toluene were placed in a flask. Under atmosphere of hydrogen, the resulting mixture was stirred with heating at 100° C. for 24 hours. The reaction mixture was filtered, and the solvent in the filtrate was removed under pressure, thereby to obtain a crude product of compound (i). This crude product was purified by column chromatography (hexane), whereby 42.5 g (yield: 91%) of compound (i) was obtained.

(3) Synthesis of compound (j)

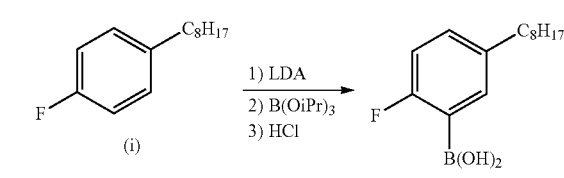

20 g (96.0 mmol) of the compound (i) and dehydrated tetrahydrofuran were placed in a flask, followed by cooling to −70° C. To the resulting mixture, 133 ml (144.0 mmol) of 1.08M-lithium diisopropylamide was added dropwise. The mixture was stirred at −70° C. for 1.5 hours. 36.1 g (192.0 mmol) of triisopropyl borate was added dropwise, and the temperature was elevated to room temperature, followed by stirring for 4 hours. An aqueous hydrochloric acid solution was added to the reaction mixture, and extracted with dichloromethane. The solvent in the organic phase was removed under reduced pressure, thereby to obtain a crude product of the compound 6). This crude product was purified by column chromatography (hexane: acetone), whereby 13.4 g (yield: 55%) of compound 6) was obtained.

(4) Synthesis of Compound (k)

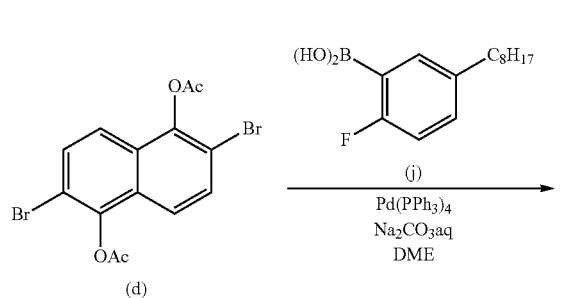

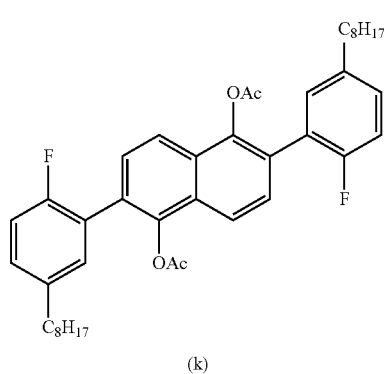

6.0 g (15.1 mmol) of the compound (d), 8.0 g (31.7 mmol) of the compound (j), 250 ml of dimethoxyethane, 6.4 g (60.4 mmol) of sodium carbonate, 250 ml of pure water and 0.87 g (0.75 mmol) of tetrakis(triphenylphosphine)palladium (0) were placed in a flask. The resulting mixture was stirred with heating at 80° C. for 3.5 hours. Pure water was added to the reaction mixture, and extracted with dichloromethane. The solvent in the organic phase was removed under reduced pressure, thereby to obtain a crude product of the compound (k). This crude product was purified by column chromatography (hexane:ethyl acetate), whereby 4.8 g (yield: 48%) of compound (k) was obtained.

(6) Synthesis of Compound (A-23)

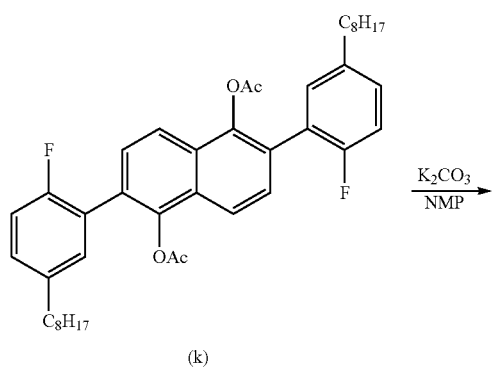

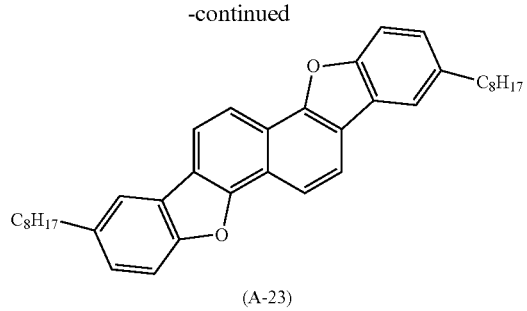

4.7 g (7.1 mmol) of the compound (k), 5.9 g (42.9 mmol) of potassium carbonate and 100 ml of dehydrated 1-methyl-2-pyrrolidone were placed. The resulting mixture was stirred with heating at 170° C. for 2 hours. The reaction mixture was cooled, and precipitated solids were filtrated and washed with pure water, thereby to obtain a crude product of compound (A-23). The resulting crude product was purified by re-crystallization and sublimation, whereby 0.76 g (yield: 20%) of compound (A-23) was obtained.

The product was identified as the intended product by the FD-MS (Field Desorption Mass Spectrometry) analysis. The measurement results of the FD-MS are shown below.

FD-MS, calcd for $C_{38}H_{44}O_2$=532, found, m/z=532 (M+, 100)

Example 4

Production of an Organic Thin Film Transistor by Deposition Process

An organic thin film transistor was produced by the following procedures.

A glass substrate was subjected to ultrasonic cleaning in neutral detergent, pure water, acetone and ethanol, each for 30 minutes. After that, gold (Au) was deposited with a thickness of 40 nm by sputtering to form a gate electrode. Subsequently, this substrate was mounted in the film-formation part of a heating CVD apparatus.

On the other hand, 250 mg of polyparaxylene derivative [polyparaxylene chloride (Parylene)] (diX-C, manufactured by DAISAN KASEI CO., LTD.) as a raw material for an insulator layer was put in a petri dish and set in the raw material evaporation part. The heating CVD apparatus was vacuumed using a vacuum pump to reduce the pressure to 5 Pa. After that, the evaporation part was heated to 180° C., the polymerizing part was heated to 680° C., and then the both parts are left for 2 hours. As a result, a 1 μm-thick insulating layer was formed on the gate electrode.

Subsequently, the substrate was provided in a vacuum evaporation deposition apparatus (EX-400, manufactured by ULVAC, Inc.), and the above compound (A-75) was formed into a 50 nm-thick film as an organic semiconductor layer at a deposition speed of 0.05 nm/s. Subsequently, gold was formed into a 50 nm-thick film through a metal mask, whereby a source electrode and a drain electrode which were not in contact with each other were formed that the interval therebetween (channel length L) became 75 μm. Film formation was conducted such that the width between the source electrode and the drain electrode (channel width W) became 5 mm, whereby an organic thin film transistor was produced (see FIG. 3).

A gate voltage ($V_G$) of −70V was applied to the gate electrode in the organic thin film transistor obtained, whereby current was flown between the source electrode and the drain electrode by applying a voltage. In this case, holes were induced in the channel region (between the source electrode and the drain electrode), thereby to lead to p-type driving. As a result, the field effect mobility μ of the holes was calculated by the following formula (A), and found to be 1.0 cm²/Vs.

$$I_D = (W/2L) \cdot C\mu \cdot (V_G - V_T)^2 \quad (A)$$

wherein $I_D$ is current flowing between the source electrode and the drain electrode, W is the channel width, L is the channel length, C is the electric capacitance per unit area of the gate insulating layer, $V_T$ is a gate threshold voltage and $V_G$ is a gate voltage.

Example 5

Production of an Organic Thin Film Transistor by Coating Process

The substrate was cleaned, and a film for the gate electrode and the insulating layer were formed in the same manner as in Example 4. Subsequently, the compound (A-8) was dissolved in toluene in a concentration of 0.4 wt %. The solution was formed into a film on the substrate with the insulating layer by a spin coater (1H-D7; produced by MIKASA CO., LTD.) The resulting substrate was dried at 80° C. in a nitrogen atmosphere to obtain an organic semiconductor layer. By forming gold (Au) into a 50 nm-film through a metal mask, a source electrode and a drain electrode which were not in contact with each other were formed whereby an organic thin film transistor was produced. For the organic thin film transistor obtained, a gate voltage ($V_G$) of −70V was applied, thereby to lead to p-type driving in the same manner as in Example 4. A current on/off between the source electrode and the drain electrode was measured to calculate the field effect mobility μ of a hole. The results were shown in Table 1.

Example 6

Production of an Organic Thin Film Transistor by Coating Process

An organic thin film transistor was produced in the same manner as in Example 5, except that the compound (A-23) was used instead of the compound (A-8) as the material for the organic semiconductor layer. For the organic thin film transistor obtained, a gate voltage ($V_G$) of −70V was applied, thereby to lead to p-type driving in the same manner as in Example 4. A current on/off between the source electrode and the drain electrode was measured to calculate the field effect mobility μ of a hole. The results were shown in Table 1.

Comparative Example 1

Organic Thin Film Transistor

An organic thin film transistor was produced by the following procedures. First, the surface of the Si substrate (p-type, also serving as a gate electrode having a specific resistance of 1 Ωcm) was oxidized by the thermal oxidation method, thereby a thermally-oxidized film having a thickness of 30 nm was formed on the substrate to serve as an insulator layer. Further, an SiO₂ film formed on one side of the substrate was completely removed by dry etching. On this film, gold (Au) was formed by sputtering into a film of 100 nm to provide an electrode. This substrate was subjected to ultra-sonic cleaning in neutral detergent, pure water, acetone and ethanol, each for 30 minutes. Further, the substrate was subjected to ozone cleaning.

Subsequently, the substrate was provided in a vacuum evaporation deposition apparatus (EX-400, manufactured by ULVAC, Inc.), and the comparative compound shown below was formed into a 50 nm-thick film as an organic semiconductor layer at a deposition speed of 0.05 nm/s. Subsequently, gold was formed into a 50 nm-thick film through a metal mask, whereby a source electrode and a drain electrode which were not in contact with each other were formed such that the interval therebetween (channel length L) became 75 μm. Film formation was conducted such that the width between the source electrode and the drain electrode (channel width W) became 5 mm, whereby an organic thin film transistor was produced (see FIG. 3).

Com. Compound (1)

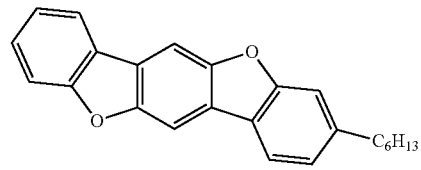

For the organic thin film transistor obtained, a gate voltage ($V_G$) of −70V was applied, thereby to lead to p-type driving in the same manner as in Example 4. A current on/off between the source electrode and the drain electrode was measured to calculate the field effect mobility μ of a hole. The results were shown in Table 1.

TABLE 1

| | Organic semiconductor layer | Type of transistor | Field effect mobility (cm²/Vs) |
|---|---|---|---|
| Example 4 | Compound A-75 | p type | 1.0 |
| Example 5 | Compound A-8 | p type | 1.1 |
| Example 6 | Compound A-23 | p type | 1.2 |
| Com. Ex. 1 | Com. Compound (1) | p type | 0.2 |

From Table 1, it is clearly understood that the organic TFT of the invention has a high carrier mobility and the compound of the invention is useful as a semiconductor material of an organic TFT.

Example 7

Synthesis of Compound (A-4)

(1) Synthesis of Compound (l)

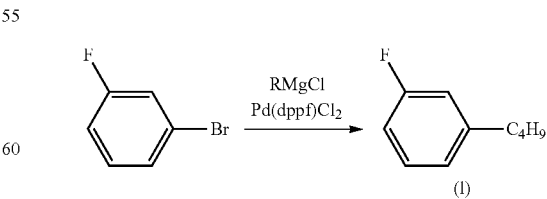

25.0 g (143 mmol) of 1-bromo-3-fluorobenzene was placed in a flask, and inside of the flask was replaced with nitrogen. 30 ml of dehydrated THF and 0.82 g (1.0 mmol) of Pd(dppf)Cl₂·CH₂Cl₂ were added. Subsequently, 110 ml (0.22 mol) of 2M-butylmagnesium chloride was added. The resulting mixture was stirred at room temperature for 30 minutes, followed by stirring with heating at 50° C. for 7 hours. The reaction mixture was cooled. Methanol, pure water, an aqueous saturated NH$_4$Cl solution and an aqueous HCl solution were added, and extracted with hexane. An organic phase was washed with saturated saline, dried with MgSO$_4$, and the solvent was removed, whereby a crude product of compound (l) was obtained.

This crude product was purified by column chromatography, whereby 17.8 g (yield: 82%) of compound (l) was obtained.

(2) Synthesis of Compound (m)

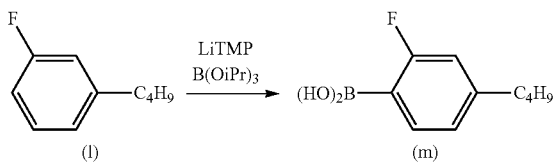

In a nitrogen-replaced flask, 21.5 g (0.152 mol) of 2,2,6,6-tetramethylpiperidine and 200 ml of dehydrated THF were added, and the resulting mixture was cooled to −56° C. 91 ml (0.152 mol) of 1.67M-normalbutyllithium was added, followed by stirring at −24° C. for 30 minutes. The mixture was then cooled to −75° C. 54 ml (0.234 mol) of triisopropyl borate was added dropwise, followed by stirring for 5 minutes. 17.8 g (0.177 mol) of the compound (I) was dissolved in 20 ml of dehydrated THF, and the resulting solution was added dropwise. The cooling bath was removed, the mixture was stirred at room temperature for 10 hours. The reaction mixture was cooled, and an aqueous 5% HCl solution was added, followed by stirring at room temperature for 30 minutes. Then, it was extracted with ethyl acetate, and an organic phase was washed with saturated brine, dried over MgSO$_4$, the solvent was removed, whereby a crude product of the compound (m) was obtained.

This crude product was purified by column chromatography, whereby 18.3 g (yield: 80%) of compound (m) was obtained.

(3) Synthesis of Compound (A-4)

Compound (A-4) was synthesized in the same manner as in Example 1, except that compound (m) was used instead of compound (c).

The compound was identified as an intended product by the FD-MS (Field Desorption Mass Spectrometry) analysis. The measurement results of the FD-MS are shown below.

FD-MS, calcd for $C_{30}H_{28}O_2$=420, found, m/z=420 (M$^+$, 100)

Examples 8 to 14

Synthesis of Compounds (A-5), (A-6), (A-7), (A-9), (A-10), (A-11) and (A-12)

In the same manner as in Example 1 or Example 7, boronic acid corresponding to each of these was synthesized. Using the boronic acid thus obtained, compounds (A-5), (A-6), (A-7), (A-9), (A-10), (A-11) and (A-12) were synthesized in the same manner as in Example 1.

The compound was identified as an intended product by the FD-MS (Field Desorption Mass Spectrometry) analysis. The measurement results of the FD-MS are shown below.

Compound (A-5)
FD-MS, calcd for $C_{32}H_{32}O_2$=448, found, m/z=448 (M$^+$, 100)
Compound (A-6)
FD-MS, calcd for $C_{34}H_{36}O_2$=476, found, m/z=476 (M$^+$, 100)
Compound (A-7)
FD-MS, calcd for $C_{36}H_{40}O_2$=504, found, m/z=504 (M$^+$, 100)
Compound (A-9)
FD-MS, calcd for $C_{40}H_{48}O_2$=560, found, m/z=560 (M$^+$, 100)
Compound (A-10)
FD-MS, calcd for $C_{42}H_{52}O_2$=588, found, m/z=588 (M$^+$, 100)
Compound (A-11)
FD-MS, calcd for $C_{44}H_{56}O_2$=616, found, m/z=616 (M$^+$, 100)
Compound (A-12)
FD-MS, calcd for $C_{46}H_{60}O_2$=644, found, m/z=644 (M$^+$, 100)

Example 15

Synthesis of Compound (A-19)

Synthesis of Compound (n)

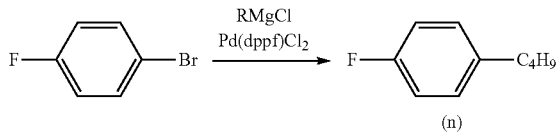

16.0 g (91 mmol) of 1-bromo-4-fluorobenzene was placed in a flask, and inside of the flask was replaced with nitrogen. 20 ml of dehydrated THF and 0.52 g (0.64 mmol) of Pd(dppf)Cl$_2$.CH$_2$Cl$_2$ were added. Subsequently, 125 ml (0.114 mol) of 0.91M-butylmagnesium chloride was added. The resulting mixture was stirred at room temperature for 20 minutes, followed by stirring at 60° C. for 8 hours. The reaction mixture was cooled. Methanol, pure water and aqueous HCl solution were added, and extracted with hexane. An organic phase was washed with saturated brine, dried over MgSO$_4$, and the solvent was removed, whereby a crude product of compound (n) was obtained.

This crude product was purified by column chromatography, whereby 6.9 g (yield: 50%) of compound (n) was obtained.

Compound (A-19) was synthesized in the same manner as in Example 3 (Synthesis of compound (A-23)), except that compound (n) was used instead of compound (I).

The compound was identified as an intended product by the FD-MS (Field Desorption Mass Spectrometry) analysis. The measurement results of the FD-MS are shown below.

FD-MS, calcd for $C_{30}H_{28}O_2$=420, found, m/z=420 (M$^+$, 100)

Examples 16 to 22

Synthesis of Compounds (A-20), (A-21), (A-22), (A-24), (A-25), (A-26) and (A-27)

In the same manner as in Example 3 or Example 15, boronic acid corresponding to each of these was synthesized.

Using the boronic acid thus obtained, compounds (A-20), (A-21), (A-22), (A-24), (A-25), (A-26) and (A-27) were synthesized in the same manner as in Example 3.

The compound was identified as an intended product by the FD-MS (Field Desorption Mass Spectrometry) analysis. The measurement results of the FD-MS are shown below.

Compound (A-20)
FD-MS, calcd for $C_{32}H_{32}O_2$=448, found, m/z=448 (M$^+$, 100)

Compound (A-21)
FD-MS, calcd for $C_{34}H_{36}O_2$=476, found, m/z=476 (M$^+$, 100)

Compound (A-22)
FD-MS, calcd for $C_{36}H_{40}O_2$=504, found, m/z=504 (M$^+$, 100)

Compound (A-24)
FD-MS, calcd for $C_{40}H_{48}O_2$=560, found, m/z=560 (M$^+$, 100)

Compound (A-25)
FD-MS, calcd for $C_{42}H_{52}O_2$=588, found, m/z=588 (M$^+$, 100)

Compound (A-26)
FD-MS, calcd for $C_{44}H_{56}O_2$=616, found, m/z=616 (M$^+$, 100)

Compound (A-27)
FD-MS, calcd for $C_{46}H_{60}O_2$=644, found, m/z=644 (M$^+$, 100)

Example 23

Synthesis of Compound (A-48)

Synthesis of Compound (o)

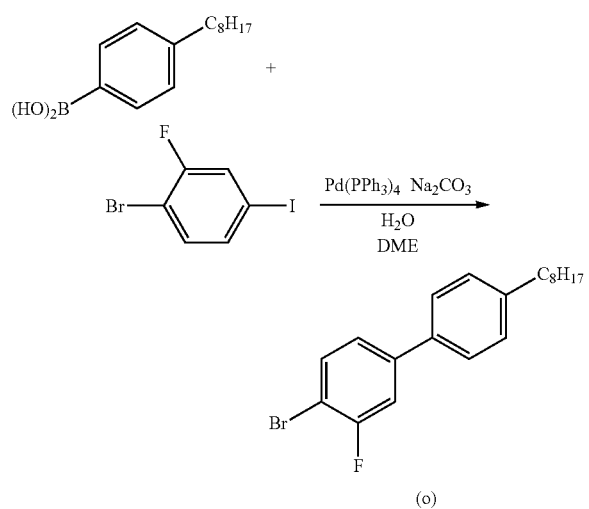

14.3 g (61.0 mmol) of 4-octylphenylboronic acid, 16.7 g (55.5 mmol) of 1-bromo-2-fluoro-4-iodobenzene, 200 ml of dimethoxyethane, 19.4 g (0.183 mol) of sodium carbonate, 200 ml of pure water, 1.0 g (0.86 mmol) of tetrakis(phenylphosphine)palladium (0) were placed in a flask. The resulting mixture was stirred at 60° C. for 8 hours. Pure water was added to the reaction mixture and extracted with dichloromethane. The solvent in an organic phase was removed with hexane, whereby a crude product of compound (o) was obtained.

This crude product was purified by column chromatography, whereby 18.2 g (yield: 90%) of compound (o) was obtained.

Compound (A-48) was synthesized in the same manner as in Example 1, except that the compound (o) was used instead of the compound (b).

The compound was identified as an intended product by the FD-MS (Field Desorption Mass Spectrometry) analysis. The measurement results of the FD-MS are shown below.

FD-MS, calcd for $C_{50}H_{52}O_2$=684, found, m/z=684 (M$^+$, 100)

Example 24

Synthesis of Compound (A-50)

(1) Synthesis of Compound (p)

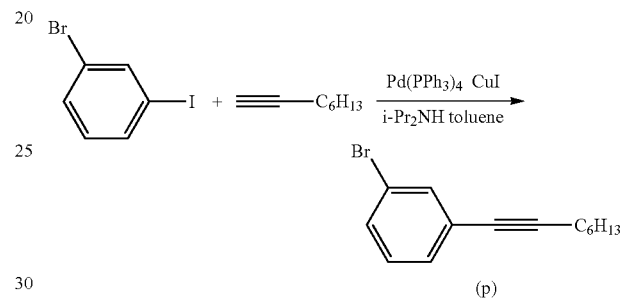

50.0 g (0.177 mol) of 1-fluoro-4-iodobenzene 1.0 g (0.86 mmol) of tetrakis(triphenylphosphine)palladium (0), 0.33 g (1.73 mmol) of copper iodide (I) and 350 ml of diisopropylamine were placed in a flask. 21.0 g (0.194 mol) of 1-octyne and 350 ml of dehydrated toluene were added thereto. The resulting mixture was stirred at 60° C. for 6.5 hours. The reaction mixture was filtered, and the solvent in the filtrate was removed under reduced pressure and purified by column chromatography to obtain 51.6 g of a crude product of compound (p). This crude product was used in the subsequent reaction.

(2) Synthesis of Compound (q)

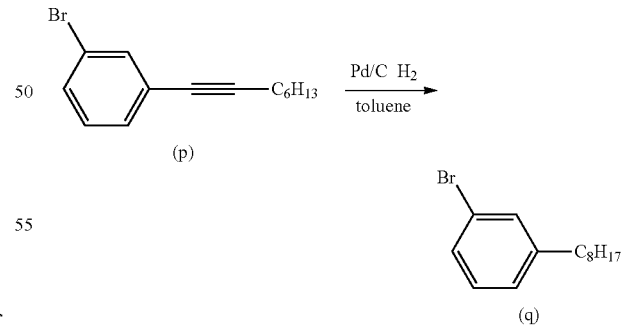

51.6 g (0.177 mol) of the compound (p), 1.0 g of palladium/carbon (Pd 5%) and dehydrated toluene were placed in a flask. Under atmosphere of hydrogen, the resulting mixture was stirred with heating at 100° C. for 24 hours. The reaction mixture was filtered, and the solvent in the filtrate was removed under reduced pressure, thereby to obtain a crude product of compound (q).

This crude product was purified by column chromatography, whereby 43.1 g (yield: 92%) of compound (q) was obtained.

(3) Synthesis of Compound (r)

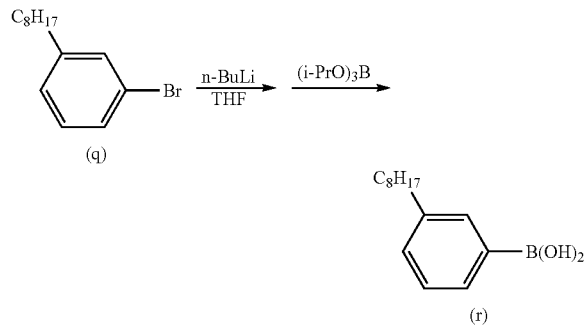

25.0 g (92.9 mmol) of the compound (q), dehydrated tetrahydrofuran (200 ml) and dehydrated toluene (200 ml) were placed in a flask, followed by cooling to −78° C. To the resulting mixture, 89 ml (139 mmol) of 1.56M-normalbutyl-lithium was added dropwise. The mixture was stirred at −78° C. for 1.5 hours. 35.0 g (186 mmol) of triisopropyl borate was added dropwise, and the temperature was elevated to room temperature, followed by stirring for 4 hours. An aqueous hydrochloric acid solution was added to the reaction mixture, and extracted with ethyl acetate. The solvent in the organic phase was removed under reduced pressure, thereby to obtain a crude product of the compound (r).

This crude product was purified by column chromatography, whereby 18.1 g (yield: 83%) of compound (r) was obtained.

Compound (A-50) was synthesized in the same manner as in Example 23, except that the compound (r) was used instead of 4-octylphenylboronic acid in Example 23.

The compound was identified as an intended product by the FD-MS (Field Desorption Mass Spectrometry) analysis. The measurement results of the FD-MS are shown below.

FD-MS, calcd for $C_{50}H_{52}O_2$=684, found, m/z=684 (M+, 100)

Examples 25 to 38

Production of an Organic Thin Film Transistor by Coating Process

Organic thin film transistors were produced in the same manner as in Example 5, except that that the compounds (A-4), (A-5), (A-6), (A-7), (A-9), (A-10), (A-11), (A-12), (A-19), (A-20), (A-21), (A-22), (A-48) and (A-50) were respectively used instead of the compound (A-8) as the material for the organic semiconductor layer. For the organic thin film transistors obtained, a gate voltage ($V_G$) of −70V was applied, thereby to lead to p-type driving in the same manner as in Example 4. A current on/off between the source electrode and the drain electrode was measured to calculate the field effect mobility μ of a hole. The results were shown in Table 2.

TABLE 2

| | Organic semiconductor layer | Type of transistor | Field effect mobility ($cm^2/Vs$) |
|---|---|---|---|
| Example 25 | Compound A-4 | p type | 1.1 |
| Example 26 | Compound A-5 | p type | 1.3 |
| Example 27 | Compound A-6 | p type | 0.5 |
| Example 28 | Compound A-7 | p type | 0.8 |
| Example 29 | Compound A-9 | p type | 0.8 |
| Example 30 | Compound A-10 | p type | 0.4 |
| Example 31 | Compound A-11 | p type | 0.4 |
| Example 32 | Compound A-12 | p type | 0.7 |
| Example 33 | Compound A-19 | p type | 1.2 |
| Example 34 | Compound A-20 | p type | 1.4 |
| Example 35 | Compound A-21 | p type | 1.1 |
| Example 36 | Compound A-22 | p type | 1.5 |
| Example 37 | Compound A-48 | p type | 0.3 |
| Example 38 | Compound A-50 | p type | 0.4 |
| Com. Ex. 1 | Com. Compound (1) | p type | 0.2 |

From the results shown in Table 2, it can be assumed that transistors can have excellent transistor performance even though the compounds (A-24), (A-25), (A-26) and (A-27) are used, since these compounds have the similar structures to those of the compounds in Examples 25 to 38.

Industrial Applicability

As explained hereinabove, the polycyclic fused-ring compound of the invention can be used as a material for an organic thin film transistor. Since the polycyclic fused-ring compound of the invention has a high carrier mobility as the material for the organic semiconductor layer, the organic thin film transistor of the invention has a high response speed (driving speed), i.e. has excellent transistor performance. It can be utilized as an organic thin film light-emitting transistor which can emit light.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A compound for an organic thin film transistor represented by the following formula (1):

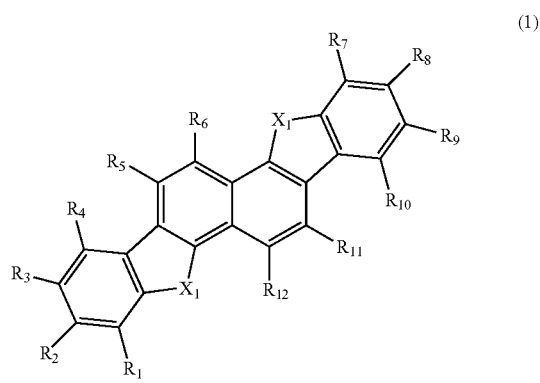

wherein $X_1$s are independently an oxygen atom or a group represented by N—$R_{13}$;

$R_1$ to $R_{13}$ are independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent; and when $X_1$s are both groups represented by N—$R_{13}$, two $R_{13}$s may be the same or different.

2. A polycyclic ring-fused compound represented by the following formula (2):

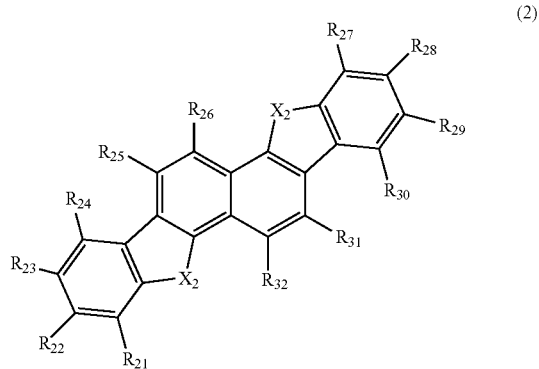

(2)

wherein $X_2$s are independently an oxygen atom or a group represented by N—$R_{33}$;

$R_{21}$ to $R_{32}$ are independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent;

$R_{33}$ is a halogen atom, an alkyl group having 1 to 30 carbon atoms, a haloalkyl group having 1 to 30 carbon atoms, an alkoxy group having 1 to 30 carbon atoms, a haloalkoxy group 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein the alkyl groups may be combined with each other to form a ring structure containing a nitrogen atom, an alkylsulfonyl group having 1 to 30 carbon atoms, a haloalkylsulfonyl group having 1 to 30 carbon atoms, an aryl group having 3 to 60 carbon atoms, an alkylsilyl group having 3 to 20 carbon atoms, an alkylsilylethynyl group having 5 to 60 carbon atoms, an arylamino group having 3 to 60 carbon atoms, a diarylamino group having 6 to 120 carbon atoms or a cyano group, which each may have a substituent; and when $X_2$s are both groups represented by N—$R_{33}$, two $R_{33}$s may be the same or different.

3. A material for an organic thin film transistor comprising the compound represented by the formula (1) according to claim 1.

4. An organic thin film transistor comprising at least three terminals of a gate electrode, a source electrode and a drain electrode, an insulating layer and an organic semiconductor layer provided on a substrate, current flowing between the source electrode and the drain electrode being controlled by applying a voltage to the gate electrode, the organic semiconductor layer comprising the compound represented by the formula (1) according to claim 1.

5. The organic thin film transistor according to claim 4, wherein light is emitted by utilizing current flowing between the source electrode and the drain electrode and emission is controlled by applying a voltage to the gate electrode.

6. The organic thin film transistor according to claim 5, wherein one of the source electrode and the drain electrode comprises a material having a work function of 4.2 eV or more and the other electrode comprises a material having a work function of 4.3 eV or less.

7. The organic thin film transistor according to claim 4, which further comprises a buffer layer between the source and drain electrodes, and the organic semiconductor layer.

8. An apparatus comprising the organic thin film transistor according to claim 4.

9. A material for an organic thin film transistor comprising the compound represented by the formula (2) according to claim 2.

10. An organic thin film transistor comprising at least three terminals of a gate electrode, a source electrode and a drain electrode, an insulating layer and an organic semiconductor layer provided on a substrate, current flowing between the source electrode and the drain electrode being controlled by applying a voltage to the gate electrode, the organic semiconductor layer comprising the compound represented by the formula (2) according to claim 2.

11. The organic thin film transistor according to claim 10, wherein light is emitted by utilizing current flowing between the source electrode and the drain electrode and emission is controlled by applying a voltage to the gate electrode.

12. The organic thin film transistor according to claim 11, wherein one of the source electrode and the drain electrode comprises a material having a work function of 4.2 eV or more and the other electrode comprises a material having a work function of 4.3 eV or less.

13. The organic thin film transistor according to claim 10, which further comprises a buffer layer between the source and drain electrodes, and the organic semiconductor layer.

14. An apparatus comprising the organic thin film transistor according to claim 10.

* * * * *